US010058504B2

(12) United States Patent
Gutierro Aduriz et al.

(10) Patent No.: US 10,058,504 B2
(45) Date of Patent: *Aug. 28, 2018

(54) METHODS FOR THE PREPARATION OF INJECTABLE DEPOT COMPOSITIONS

(71) Applicant: LABORATORIOS FARMACEUTICOS ROVI, S.A., Madrid (ES)

(72) Inventors: Ibon Gutierro Aduriz, Madrid (ES); Maria Teresa Gomez Ochoa, Madrid (ES)

(73) Assignee: LABORATORIOS FARMACEUTICOS ROVI, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/690,707

(22) Filed: Nov. 30, 2012

(65) Prior Publication Data
US 2013/0177603 A1 Jul. 11, 2013

(30) Foreign Application Priority Data
May 31, 2010 (EP) .................................... 10382153

(51) Int. Cl.
| A61K 9/00 | (2006.01) |
| A61K 47/34 | (2017.01) |
| A61K 31/551 | (2006.01) |
| A61K 31/4468 | (2006.01) |
| A61K 31/519 | (2006.01) |
| A61K 31/4196 | (2006.01) |

(52) U.S. Cl.
CPC .......... *A61K 9/0002* (2013.01); *A61K 9/0024* (2013.01); *A61K 31/4196* (2013.01); *A61K 31/4468* (2013.01); *A61K 31/519* (2013.01); *A61K 31/551* (2013.01); *A61K 47/34* (2013.01)

(58) Field of Classification Search
None
See application file for complete search history.

(56) References Cited

U.S. PATENT DOCUMENTS

| 3,636,956 A | 1/1972 | Ethicon |
| 3,773,919 A | 11/1973 | Dupont |
| 4,389,330 A | 6/1983 | Stolle |
| 4,523,591 A | 6/1985 | Kaplan |
| 4,530,840 A | 7/1985 | Stolle |
| 4,938,763 A | 7/1990 | Dunn |
| 5,620,700 A | 4/1997 | Alza |
| 5,620,770 A | 4/1997 | Bergren |
| 5,688,801 A | 11/1997 | Janssen |
| 5,770,231 A | 6/1998 | Alkermes |
| 6,143,314 A | 11/2000 | Chandrashekar |
| 6,331,311 B1 | 12/2001 | Alza |
| 6,528,080 B2 | 3/2003 | Dunn |
| 6,565,874 B1 | 5/2003 | Dunn |
| 6,630,155 B1 | 10/2003 | Chandrashekar |
| 6,673,767 B1 | 1/2004 | Alza |
| 6,803,055 B2 | 10/2004 | Mesens |
| 7,118,763 B2 | 10/2006 | Mesens |
| 8,221,778 B2 | 7/2012 | Siegel |
| 2002/0023409 A1* | 2/2002 | Py .................................. 53/426 |
| 2003/0165571 A1 | 9/2003 | Alkermes |
| 2004/0010224 A1* | 1/2004 | Bodmeier ....................... 604/82 |
| 2004/0247870 A1 | 12/2004 | Brown |
| 2005/0003007 A1 | 1/2005 | Boix |
| 2005/0025828 A1 | 2/2005 | Alkermes |
| 2006/0121085 A1 | 6/2006 | Warren |
| 2006/0210604 A1 | 9/2006 | Dadey |
| 2007/0003596 A1* | 1/2007 | Tittelbach et al. ........... 424/426 |
| 2008/0287464 A1* | 11/2008 | Wright et al. ........... 514/259.41 |
| 2009/0264491 A1* | 10/2009 | McKay et al. ................ 514/401 |
| 2010/0021544 A1* | 1/2010 | Bourges et al. .............. 424/486 |
| 2010/0266655 A1 | 10/2010 | Dadey |
| 2013/0171202 A1 | 7/2013 | Gutierro Aduriz et al. |
| 2015/0147398 A1 | 5/2015 | Gutierro Aduriz et al. |
| 2015/0150791 A1 | 6/2015 | Gutierro Aduriz et al. |
| 2015/0196485 A1 | 7/2015 | Franco Rodriguez et al. |

FOREIGN PATENT DOCUMENTS

| WO | 99/36071 A1 | 7/1999 |
| WO | 02/38185 A2 | 5/2002 |
| WO | 2007/123456 * | 4/2007 |

(Continued)

OTHER PUBLICATIONS

Sigma-Aldrich. Dimethyl sulfoxide [online]. Sigma-Aldrich, Jan. 12, 2009. [retrieved on: Feb. 7, 2014]. Retrieved from the internet: <URL:http://www.sigmaaldrich.com/chemistry/solvents/dimethyl-sulfoxide-center.html>.*
Product Block. Risperidone [online]. Santa Cruz Biotechnology, 2014 [retrieved on Feb. 7, 2014]. Retrieved from the internet: <URL: http://www.scbt.com/datasheet-204881-risperidone.html>.*
Wang et al. ("Design of a long-term antipsychotic in situ forming implant and its release control method and mechanism", Int. J. Pharm., May 10, 2012;427(2):284-92.
Maryott et al. (Table of Dielectric Constants of Pure Liquids, National Bureau of Standards, Circular No. 514, Aug. 10, 1951).

(Continued)

*Primary Examiner* — Katherine Peebles
(74) *Attorney, Agent, or Firm* — Innovar, L.L.C.; Rick Matos

(57) ABSTRACT

Injectable depot compositions, comprising a biocompatible polymer which is a polymer or copolymer based on lactic acid and/or lactic acid plus glycolic acid having a monomer ratio of lactic to glycolic acid in the range from 48:52 to 100:0, a water-miscible solvent having a dipole moment of about 3.7-4.5 D and a dielectric constant of between 30 and 50, and a drug, were found suitable for forming in-situ biodegradable implants which can evoke therapeutic drug plasma levels from the first day and for at least 14 days.

13 Claims, 24 Drawing Sheets

(56) References Cited

FOREIGN PATENT DOCUMENTS

| WO | WO/2007/041410 | * | 4/2007 |
|----|----------------|---|--------|
| WO | WO/2008/059058 | * | 1/2008 |
| WO | 2008/123456 | * | 5/2008 |
| WO | 2008/123456 | * | 12/2008 |
| WO | WO/2008/153611 | * | 12/2008 |
| WO | 2009/060473 A2 | | 5/2009 |
| WO | 2011/151355 A1 | | 12/2011 |
| WO | 2013/178811 A1 | | 12/2013 |
| WO | 2013/178812 A1 | | 12/2013 |
| WO | 2014/19972 A1 | | 2/2014 |

OTHER PUBLICATIONS

Gouw et al. (Physical Properties of Triglycerides IV. Dielectric Constant, Fette Seifen Anstrichmittel, (1967), 69(4), 223-226).
Lide (Properties of Common Laboratory Solvents, CRC Handbook of Chemistry and Physics 84th Ed., 2003-2004, Sect. 15-14, CRC Press, New York).
Yapar et al. ("Effects of solvent combinations on drug release from injectable phase sensitive liquid implants", in Turk. J. Pharm. Sci. (2010), 7(1), 49-56).
Prashanth et a. ("Formulation and characterization of in situ implant of octeotride acetate", in Int. J. Pharm. (2013), 3(3), 565-573).
Calis et al. ("Influence of irradiation sterilization on poly(lactide-co-glycolide) microspheres containing anti-inflammatory drugs", in Il Farmaco (2002), 57, 55-62).

* cited by examiner

METHODS FOR THE PREPARATION OF INJECTABLE DEPOT COMPOSITIONS

CROSS-REFERENCE TO EARLIER FILED APPLICATIONS

The present application claims the benefit of PCT/EP2011/059001, filed May 31, 2011, which claims the benefit of EP 10382153.4 filed May 31, 2010, the entire disclosures of which are hereby incorporated by reference.

FIELD OF THE INVENTION

The present invention relates to implantable compositions that form extended release drug-delivery devices comprising certain drugs. Specifically, the present invention is related to injectable compositions that form biodegradable implants in-situ after administration to a subject.

BACKGROUND OF THE INVENTION

Sustained-release delivery devices are usually a very satisfactory administration method for certain drugs, in particular (but not limited to) drugs for patients in need of a treatment for diseases such as schizophrenia. Some treatments for disorders usually involve daily oral tablets or solutions. However, one of the intrinsic problems of these treatments is the dissociation (non-compliance) of some schizophrenic patients from the treatment, especially when therapy requires daily administration. Non-compliance leads to irregular or inconstant treatments and favors the appearance of psychotic crisis or episodes. Moreover, oral tablet therapy gives rise to high fluctuations in the plasma levels (measured as the difference between Cmax and Cmin) in patients, therefore usually affecting the patient's mood. On the contrary, administration of sustained-release delivery devices should provide adequate drug delivery to a patient for extended periods of time with just one dose and without the need of caregivers to pay attention to a daily medication, thereby providing more homogeneous plasma levels in the patient.

One of the most common ways to administer certain drugs presently is through the use of depot injections. Depot injections allow careful control of drug usage (as opposed to orally administered drugs) and ensure regular contact between the caregivers' team and the patient, where overall treatment efficacy and/or side effects may be identified. Furthermore, it is easy to identify defaulters (non-compliant patients) and prepare interventions. However, in situ forming implants currently described in the state of the art cannot properly control drug release from the implant, and fail to provide therapeutic plasma levels sufficient for a bi-weekly administration protocol while exhibiting reasonable differences between maximum and minimum plasma concentrations.

For example, the long-acting injectable risperidone formulation, Risperdal Consta®, is the first depot atypical antipsychotic drug in the market. It is an intramuscular risperidone-containing PLGA microparticle formulation, and it is intended to deliver therapeutic levels of risperidone suitable for bi-weekly administration. However, due to the inherent lag phase of most microparticle-based products, the patient is required to supplement the first weeks with daily doses of oral risperidone after first administration. Approximately three weeks after a single intramuscular injection of Risperdal Consta® and concurrent daily doses of oral risperidone, the microspheres release sufficient risperidone in the systemic circulation that the patient can discontinue supplementation with daily doses of the oral therapy. However, this period of oral supplementation could be a risk factor of non-compliance. Also, the presence in the body of two doses at the same time could present a potential risk of adverse events, such as irregular formulation behaviour and toxicity.

The compositions and devices of the invention, on the contrary, can evoke therapeutic drug plasma levels from the first day and for at least 14 days, avoiding the need of supplementary oral daily therapy from the administration moment. These compositions can also reduce the differences between Cmax and Cmin as observed with daily-administered oral tablets and subsequently may reduce variations in the patient mood. In addition, they can also cover a period within administrations that is at least as long as the period covered by currently marketed extended-release risperidone formulations.

A biodegradable copolymer poly(DL-lactide-co-glycolide) matrix has been used in medical products, such as sutures described in U.S. Pat. No. 3,636,956 by Schneider, surgical clips and staples described in U.S. Pat. No. 4,523,591 by Kaplan et al., and drug delivery systems described in U.S. Pat. No. 3,773,919 by Boswell et al. However, most of the existing formulations using these biodegradable polymers require manufacturing of an implantable device in solid form prior to the administration into the body, which device is then inserted through an incision or is suspended in a vehicle and then injected. In such instances, the drug is incorporated into the polymer and the mixture is shaped into a certain form such as a cylinder, disc, or fibre for implantation. With such solid implants, the drug delivery system has to be inserted into the body through an incision. These incisions are sometimes larger than desired by the medical profession and occasionally lead to a reluctance of the patients to accept such an implant or drug delivery system.

U.S. Pat. No. 8,221,778 to Siegel et al. (corresponding to WO 2005/070332) discloses an implant containing risperidone (10-60% wt) and PLGA (90-40% wt) having a lactic acid to glycolic acid ratio of 50:50 to 100:0. These implants are not formed in situ.

Injectable biodegradable polymeric matrix implants based on lactic acid, glycolic acid and/or their copolymers for sustained release have already been described in the art. U.S. Pat. No. 5,620,700 issued to Berggren describes a bioerodible oligomer or polymer material containing drug for local application into a diseased tissue pocket such as a periodontal pocket. However, the material requires heating to high temperatures to become sufficiently flowable to allow the injection, so that hardening of the material after cooling to the body temperature conforms the implant.

U.S. Pat. No. 6,143,314 to Chandrashekar discloses an injectable composition that forms an implant in situ. The composition is made of drug, organic solvent and a PLGA/PEG block copolymer.

U.S. Pat. No. 6,673,767 issued to Brodbeck describes procedures to for in situ formation of biodegradable implants by using biocompatible polymers and biocompatible low water-miscible solvents. A viscous polymeric solution containing the drug, that upon injection releases the drug in a controlled manner, can be obtained through the use of low water-soluble solvents. Solvents with low water-solubility (less than 7% miscibility in water) are used as a method to reduce the release of the drug in aqueous mediums, allowing initial drug releases of 10% or lower during the first 24 hours. However, in our experience, the use of water-immiscible and/or low water-miscible solvents cannot satisfactorily control the initial in vivo release of risperidone during the first 24 hours. For example, the use of benzyl alcohol, a solvent specifically disclosed in U.S. Pat. No. 6,673,767, causes very high plasma levels of risperidone in the first 3 days and then the plasma levels decrease to very low levels in 7 days.

U.S. Pat. No. 6,331,311 issued to Brodbeck also discloses injectable depot compositions comprising a biocompatible polymer such as PLGA, a solvent such as N-methyl-2-pyrrolidone and a beneficial agent such as a drug, further comprising an emulsifying agent such as polyols. However, the compositions disclosed do not perform satisfactorily when the beneficial agent is risperidone because the use of a two-phase composition with emulsifying agents accelerates implant hydration and increases effective releasing surface area, impairing the control on the initial burst release and originating a fast decrease in drug release from the first days to the following ones. For example, a comparator composition was prepared according to the '311 patent. A container containing risperidone (150 mg), PLGA (300 mg, having an inherent viscosity of 0.32 dl/g and irradiated by $\beta$-irradiation to a dose of 25 KGy) and NMP (700 mg) was prepared. Another container containing polyvinyl alcohol in water (1 ml of a 2% wt/v). The contents of the containers were mixed, then the mixture was transferred to a syringe and injected intramuscularly (an amount equivalent to 2.5 mg risperidone) into the gluteus of New Zealand White rabbits (n=3). More than 70% of the total AUC of active moiety was released within the first 5 days after the injection. Such a formulation is unable to provide therapeutic plasma levels of risperidone for a period of at least two weeks.

U.S. Pat. No. 4,938,763, issued to Dunn et al., discloses a method for an injectable in situ forming implant. A biodegradable polymer or copolymer dissolved in a water-miscible solvent with a biologically active agent either is dissolved or dispersed within the polymeric solution. Once the polymeric solution is exposed to body fluids, the solvent diffuses and the polymer solidifies thereby entrapping the drug within the polymer matrix. Even though Dunn et al. discloses the use of water miscible solvents for obtaining in situ forming polymeric implants, it discloses a number of polymers and solvents and even proportions between the different ingredients that do not produce a satisfactory implant with the appropriate release characteristics, particularly when the implant contains risperidone as active principle. For example, a comparator composition was prepared according to the '763 patent. A container containing risperidone (50 mg) and PLGA (784 mg, monomer ratio of lactic acid to glycolic acid monomer of 75:25, and having an inherent viscosity of 0.20 dl/g was prepared. Another container containing NMP (1666 mg) was prepared. The contents of the containers were mixed. Then the mixture was transferred to a syringe and a portion (1250 mg, corresponding to 25 mg of risperidone) was injected into an aqueous liquid to determine its in vitro release profile. More than 50% of the risperidone was released within the first 2 days. Such a formulation is unable to provide therapeutic plasma levels of risperidone for a period of at least two weeks.

Another way to avoid surgery to administer these drugs is the injection of small-sized polymeric particles, microspheres or microparticles containing the respective drug. U.S. Pat. No. 4,389,330 and U.S. Pat. No. 4,530,840 describe a method for the preparation of biodegradable microparticles. U.S. Pat. No. 5,688,801 and U.S. Pat. No. 6,803,055 disclose microencapsulation of 1,2-benzazoles into polymeric particles to achieve a drug release over extended periods of time in the treatment of mental disorders. These microparticles require re-suspension into aqueous solvents prior to the injection. These formulations do not form a single (nonparticulate) solid implant.

U.S. Pat. No. 5,770,231 describes a method for producing biodegradable microparticles for sustained release of risperidone and 9-hydroxy-risperidone by dissolving the drug within an organic phase. However, the use of organic solvents that are able to dissolve the risperidone mostly or completely gives rise to very high initial plasma levels of risperidone due to the diffusion of the drug along with the diffusion of the solvent.

U.S. Pat. No. 7,118,763 describes two methods of making multi-phase sustained-release microparticle formulations based on the combination of different particle sizes or microparticles exhibiting different release profiles. The combination of two different release profiles allows the release of the drug for periods longer than two weeks. However, in practice this combination requires a mixture of particles from at least two different batches, involving the multiplication of end product specifications and increasing batch-to-batch variability. In addition, although microparticle formulations can be administered by injection, they cannot always satisfy the demand for a biodegradable implant because they sometimes present difficulties in the large-scale production. Moreover, in case of any medical complication after injection, they are much more difficult to remove from the body than implantable compositions such as those of the invention, which form a single body.

The art also discloses sustained-release delivery devices comprising a drug, PLGA as polymer and a water-miscible solvent such as n-methyl-pyrrolidone (NMP) or dimethyl sulfoxide (DMSO). However, in practice the experiments disclosed nearly in every case use NMP as solvent (WO 2004081196, WO 2001035929, WO 2008153611) or need different additives to control the initial burst (WO 2000024374, WO 2002038185, WO2008100576).

The compositions already described in the state of the art do not provide implants adequate for extended periods of treatment, such as chronic treatment compositions, kits and devices. In summary, there still exists a need of compositions and devices for sustained-released delivery systems providing a controlled, constant release of the drug from the very first day, avoiding irregular initial bursts, and showing controlled release profile during prolonged periods of time.

SUMMARY OF THE INVENTION

The present invention seeks to overcome one or more of the disadvantages of known depot formulations. Contrary to known injectable depot compositions, the compositions of the invention provide an easier method for the production of a single unit implantable device allowing constant and effective plasma levels during a period comprising from the first day up to at least 14 days. The compositions of the invention are injected as a liquid or semisolid formulation that precipitates by solvent diffusion after injection into a subject and forms a single (not multiparticulate) solid implant at an injection site. The compositions of the present invention provide an easier method for the production of an implant or single unit implantable device allowing constant and effective plasma levels during a dosing period comprising from the first day up to at least 14 days after administration, while avoiding irregular initial burst release of the drug. The compositions of the present invention exhibit satisfactory initial and continuous release profiles using DMSO as solvent and without the need of any additional additive to control the initial burst of the composition. By using N-methylpyrrolidone or DMSO as the solvent, both of which have high water solubility, the implant provides a smaller initial plasma level of drug than other injectable formulations and therefore provides a better control of the release of the drug during the first 5 days after the injection.

The compositions of the invention provide therapeutic drug plasma levels from the first day up to at least 14 days after implantation, thereby avoiding the need for supplementary oral daily therapy from within one day of the time of administration. These compositions can also reduce the fluctuations between Cmax and Cmin, especially as compared to those observed with daily administration of oral tablets. In addition, they can also cover a dosing period that is at least as long as the dosing periods covered by other known injectable extended-release formulations.

Some of the key points where the compositions of the invention show improvements over the state of the art include:
  Stability, by using a solid product for reconstitution previous to injection;
  Pharmacokinetic profile:
    Onset: The compositions of the invention provide therapeutic plasma levels from the first day after administration, avoiding the 2-3 weeks lag time that the currently marketed long-term product shows.
    Duration: The compositions of the invention may allow an increase in the interval between administrations, meaning an increase in the dosing period, as compared to currently marketed long-term product.
  Plasma levels: The compositions of the invention provide more evenly sustained plasma levels, and with lower differences between Cmax and Cmin than the currently marketed long-term product.

The present inventors have identified that the initial burst release of the drug can be satisfactorily controlled during at least 2 weeks by controlling at least one of the following parameters of the composition, either alone or in combination:
  the viscosity of the polymeric solution;
  the inherent or intrinsic viscosity of the polymer; and
  the water solubility of the active ingredient.

It should be noted that there was little recognition, if any, in the art that the above-enumerated variables would be result effective in terms of their impact upon the initial release of drug after implantation or after placement in an aqueous fluid. By adequately controlling at least some of these result effective variables, release of drug from the implant during at least the first two weeks can be precisely controlled, allowing "satisfactorily controlled" release profiles from the very first day until at least 14 days, and achieving in most cases dosing periods of more than 21 days and up to six months following a single administration.

The composition and kit, used to prepare the composition, are provided with a solid polymer or copolymer that is soluble in a solvent, which is non-toxic and water miscible, to form a liquid polymer solution, in which the drug is included. When the implantable compositions are exposed to body fluids or water, the solvent diffuses away from the polymer-drug mixture and water diffuses into the mixture where it coagulates the polymer thereby trapping or encapsulating the drug within the polymeric matrix as the composition solidifies into a single implant at the injection site. The release of drug follows the general characteristics for diffusion or dissolution of a drug from within a polymeric matrix. Drug is also released by polymer erosion/degradation. The drug (active ingredient) forms a suspension or dispersion within a biodegradable and biocompatible polymeric solution to form an injectable composition that can be administered by way of a syringe (or pump) and a needle. The composition solidifies inside the body by solvent diffusion, thereby forming the single implant at the site of injection.

One aspect of the invention provides an injectable composition as described and/or exemplified herein. The compositions of the invention comprise at least a polymer matrix, a solvent for the polymer and a drug, wherein the composition is defined by certain selected ranges and ratios of at least one of the following parameters, either alone or in combination:
  The water solubility of the drug;
  The intrinsic viscosity of the polymer; and/or
  The viscosity of the polymeric solution or injectable composition.

The invention provides an injectable composition comprising:
  a. a drug (and/or a metabolite and/or a prodrug thereof) having a water solubility of less than or about 2 mg/ml;
  b. a biocompatible polymer, which is a polymer or copolymer based on lactic acid or a copolymer of lactic acid and glycolic acid having a monomer ratio of lactic to glycolic acid in the range from 48:52 to 100:0, wherein the polymer (or copolymer) has an inherent viscosity in the range of 0.20-0.50 dl/g; and
  c. a water-miscible solvent having a dipole moment of about 3.7-4.5 D and a dielectric constant of between 30 and 50, thereby providing the injectable composition having a viscosity in the range of about 0.50 and 4.0 Pa·s.

Embodiments of the invention include those wherein: a) the drug is selected from the group consisting of fentanyl, olanzapine, risperidone and letrozole; b) the solvent is selected from the group consisting of DMSO and NMP; c) the polymer is selected from the group consisting of poly (lactic acid), poly(lactic acid-co-glycolic acid) copolymer and a combination thereof; d) the monomer ratio of the poly(lactic acid-co-glycolic acid) copolymer is in the range of about 48:52 to 100:0, and the copolymer has an inherent or intrinsic viscosity in the range of about 0.16-0.60 dl/g measured in chloroform at 25° C. and at a concentration of 0.1% wt; e) the polymer has an inherent or intrinsic viscosity in the range of about 0.20-0.50 dl/g or 0.25-0.48 dl/g, measured in chloroform at 25° C. and 0.1% concentration wt/v; f) the concentration of polymer in the injectable composition is in the range of about 20 to about 50%, about 25 to about 40%, or about 30 to about 40%, expressed as the percentage of polymer weight based on total weight of injectable composition; g) the viscosity of the injectable composition is in the range of about 0.5-7.0 Pa·s, about 0.5-4.0 Pa·s, or about 0.7-4.0 Pa·s; h) the drug (or metabolite or prodrug thereof) has a particle size where not more than 10% of the total volume of the particles is less than the range 0.1-10 µm, 0.5-10 µm or 1-10 µm, not more than the 10% of the total volume of particles is greater than the range 225-1000 µm, 225-700 µm or 225-400 µm, respectively, and the d0.5 of the size distribution is in the range of about 10-1000 µm, 20-700 µm or 40-200 µm, respectively, i) the ratio of solvent to polymer is in the range of about 4:1 to about 1:1, about 3:1 to about 1.2:1, or about 2:1 to about 1.4:1; k) the composition is injectable by hand with a syringe through a 18-22 gauge or 20-21 gauge needle; and/or l) the polymeric solution excluding drug has a viscosity in the range of about 0.5 to 3.0 Pa·s or 0.7 to 3.0 Pa·s.

Embodiments of the invention include those wherein: a) the drug is soluble, partially soluble or insoluble in the solvent; b) the solubility of the drug in the solvent is about 90 mg/ml or less, about 65 mg/ml or less, or about 10 mg/ml or less; c) a minor portion, a major portion or none of the drug is present in particulate form in the injectable composition; d) the particle size distribution of the drug expressed as volume is as follows: d0.9 about 150-400 μm, d0.5 about 40-200 μm and d0.1 about 10-60 μm; e) the mass ratio of solvent to drug is in the range of about 10:1 to about 1.5:1 f) the concentration of drug in the injectable composition is in the range of about 4% to about 40% wt or about 4% to about 25%, expressed as the percentage of the drug with respect to the total composition weight; g) the drug is present as particles, is partially dissolved in or is completely dissolved in the injectable composition prior to administration; h) the mass ratio of the amount of polymeric solution (polymer+solvent) to the amount of drug in the injectable composition ranges from about 24:1 to about 1.5:1 or about 15:1 to about 3:1.

Another aspect of the invention provides a pharmaceutical kit suitable for in situ formation of a biodegradable non-particulate solid implant in a subject in need thereof, the kit comprising: a first container comprising a drug, and/or a metabolite and/or a prodrug thereof, having a water solubility less than or about 2 mg/ml and a biocompatible polymer having an inherent viscosity in the range of about 0.20-0.50 dl/g or about 0.20-0.48 dl/g; and a second container comprising a water-miscible solvent in which the biocompatible polymer is soluble, the solvent having a dipole moment of about 3.7-4.5 D and a dielectric constant of between 30 and 50, whereby mixing of the contents of the first container with the contents of the second container affects formation of an injectable composition as described herein having a viscosity in the range of about 0.50 and 4.0 Pa·s. In some embodiments, the containers are syringes and the mixing of the contents of the first and second containers may be performed by direct or indirect connection followed by moving the plungers of the syringes forwards and backwards.

Embodiments of the invention include those wherein: a) drug is present in solid form in the container prior to mixing with the solvent; b) drug is present in particulate form or as a lyophilisate in the container prior to mixing with the solvent; c) the kit further comprises an alkaline agent; d) the mole ratio of alkaline agent to drug ranges from 1/3 to 5/2; e) the solvent, polymeric solution, drug and/or injectable composition is sterilized prior to administration; and/or f) the kit further comprises an alkaline agent in either or both containers.

Another aspect of the invention provides a method for the preparation of an injectable depot composition as described and/or exemplified herein. In some embodiments, the method comprises:
  a. mixing a biocompatible polymer, which is a polymer or copolymer-based on lactic acid and/or lactic acid plus glycolic acid having a monomer ratio of lactic to glycolic acid in the range from 48:52 to 100:0, wherein the polymer has an inherent viscosity in the range of 0.20-0.50 dl/g, with a drug, and/or a metabolite or a prodrug thereof in any combination, having a water solubility less than or about 2 mg/ml, wherein the drug is selected from the group consisting of fentanyl, olanzapine, risperidone and letrozole, to provide a mixture; and
  b. mixing the mixture obtained in step a) with a water-miscible solvent having a dipole moment of about 3.7-4.5 D and a dielectric constant of between 30 and 50 to form the injectable composition, wherein the viscosity of the polymeric solution is in the range of about 0.50 and 3.0 Pa·s. or the viscosity of the injectable composition is in the range of about 0.50 and 4.0 Pa·s.

Some embodiments of the invention include those wherein: a) the polymer and/or drug is exposed to an amount of beta-irradiation sufficient, e.g. 5 to 25 KGy, to sterilize the polymer and/or drug; b) the polymer is exposed to an amount of beta-irradiation sufficient, e.g. 10-25 KGy, to reduce the molecular weight, and thereby the intrinsic viscosity, of the polymer; and/or c) sterilizing the solvent by filtering it through a filtration medium have a nominal pore size of 0.22 microns or less.

Another aspect of the invention provides a method for the treatment of a disease, disorder or condition that is therapeutically responsive to a drug, the method comprising administering an amount of injectable composition, as defined herein, to a subject in need thereof, wherein the amount of injectable composition comprises a dose of drug sufficient to continuously provide therapeutically effective plasma levels of drug in the subject throughout a dosing period of at least 14 days or at least four weeks beginning from the day of administration.

Embodiments of the invention include those wherein: a) the composition is administered every two weeks, every three weeks, every four weeks or every five weeks during a treatment period; b) the composition provides a therapeutic plasma level of drug or other form thereof from within 24 hours after administration to at least 14 days or at least four weeks after administration; c) the plasma level of active moiety (risperidone+9-OH risperidone) ranges from about 5 to about 150 ng/ml and preferably from about 10 to about 100 ng/ml in the steady state during a dosing period; d) the implant provides an active moiety (risperidone+9-OH risperidone) plasma level within the range of about 5 to about 80 ng/ml when about 116 to about 700 mg, respectively, of the composition comprising about 25 to about 150 mg, respectively, of risperidone are administered via injection; e) the injectable composition is exposed to an aqueous fluid thereby forming a solid body which is then administered to a subject in need thereof; f) the injectable composition is formed within one month, within three weeks, within two weeks, within one week, within three days, within one day, within less than one day, within 18 hours, within 12 hours, within 6 hours, within 1 hour, within 15 minutes or within 5 minutes prior to administration to a subject; g) the injectable composition is warmed or cooled prior to administration to a subject; h) the polymer, solvent polymer solution and/or drug is sterilized prior to administration; i) sterilization comprises sterilization of the drug or polymer by exposure to beta-irradiation in the range 5-25 KGy; j) sterilization comprises sterilization of the polymer solution by filtration through a filtration medium having a nominal pore size of 0.22 microns or less; k) the composition is administered intramuscularly, intraperitoneally, intrathecally, intravaginally, subcutaneously, intracranially or intracerebrally; l) the plasma level of fentanyl ranges from about 0.2 to about 5 ng/ml and preferably from about 0.5 to about 2.5 ng/ml in the steady state during a dosing period; m) the plasma level of olanzapine ranges from about 5 to about 120 ng/ml and preferably from about 10 to about 80 ng/ml in the steady state during a dosing period; n) the plasma levels of letrozole should be sufficient to provide an in vivo suppression on serum estrogens (E1 and E2) of at least about 50% (E2, estradiol) and 70% (E1, estrone) and preferably of at least about 60% (E1) and 80% (E2) in the steady state during a dosing period. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

The specification discloses one or more embodiments that incorporate features of this invention. The scope of the present invention is not limited solely to the disclosed embodiments. The invention includes all combinations and sub-combinations of the various aspects and embodiments disclosed herein. These and other aspects of this invention will be apparent upon reference to the following detailed description, examples, claims and attached figures.

BRIEF DESCRIPTION OF THE FIGURES

The accompanying drawings, which are incorporated herein and form a part of the specification, illustrate one or more embodiments of the present invention and, together with the description, further serve to explain the principles of the present invention and to enable a person skill in the pertinent art to make and use the invention. The following drawings are given by way of illustration only, and thus are not intended to limit the complete scope of the present invention.

DETAILED DESCRIPTION OF THE INVENTION

Figure 1:
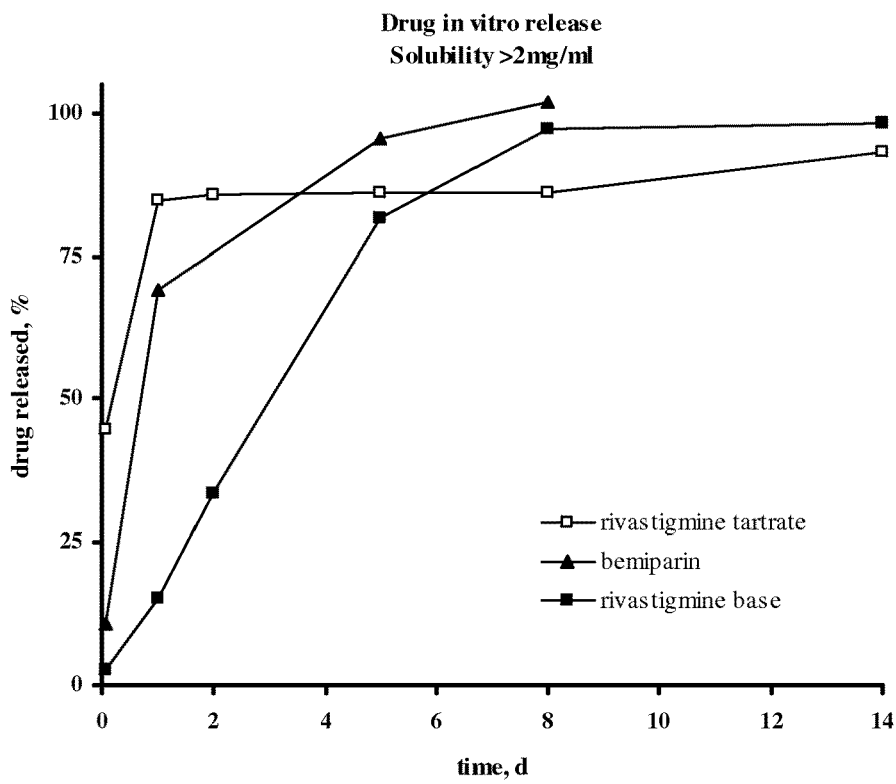
FIG. 1 depicts the release profile of Rivastigmine and Bemiparin from implants prepared according to Comparative Example 1. Results are expressed as % drug released from implants as a function of time.

As used herein and unless otherwise specified, the drug or active ingredient included in the injectable composition can be present in free base, salt, amorphous, crystalline, anhydrous, hydrate, optically pure, optically enriched or racemic forms thereof. Combinations of these various forms are also within the scope of the invention. A prodrug, metabolite or derivative of the drug can also be included.

As used herein, the term "prodrug" is taken to mean a compound that is administered in an inactive (or less than fully active) form, and is subsequently converted to an active pharmacological agent through normal metabolic processes. A prodrug serves as a type of 'precursor' to the intended drug, e.g. risperidone, olanzapine, letrozole, fentanyl or other drug.

As used herein, the term "derivative" is taken to mean a compound that is obtained by chemical modification of a parent compound such that the "derivative" includes within it almost all or all of the chemical structure of the parent (or base) compound. A derivative is a compound that is formed from a similar compound or a compound that can be imagined to arise from another compound, if one atom is replaced with another atom or group of atoms. A derivative is a compound derived or obtained from another and containing essential elements of the parent substance. A derivative is a chemical compound that may be produced from another compound of similar structure in one or more steps.

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. If not otherwise specified, the viscosity value of the polymeric solution or the injectable composition is given in Pa·s units.

The salt forms of the drugs listed herein can be obtained commercially. The salt should have a water solubility as specified herein. The salt forms of risperidone can be made according to U.S. Publication No. 20040266791, the relevant disclosure of which is hereby incorporated by reference. Suitable fentanyl salts include hydrobromide, hydrochloride, mutate, citrate, succinate, n-oxide, sulfate, malonate, acetate, phosphate dibasic, phosphate monobasic, acetate trihydrate, bi(heplafluorobutyrate), maleate, bi(methylcarbamate), bi(pentafluoropropionate), mesylate; bi(pyridine-3-carboxylate), bi(trifluoroacetate), bitartrate, chlorhydrate, fumarate, and sulfate pentahydrate salts. Suitable olanzapine salts include acid addition salts of hydrochloric acid, hydrobromic acid, sulfuric acid, nitric acid, phosphoric acid, acetic acid, propionic acid, glycolic acid, pyruvic acid, oxalic acid, malic acid, malonic acid, succinic acid, maleic acid, hydroxymaleic acid, fumaric acid, tartaric acid, citric acid, benzoic acid, cinnamic acid, mandelic acid, methanesulfonic acid, ethanesulfonic acid, p-toluenesulfonic acid, naphthalene-2-sulfonic acid, and salicylic acid. Suitable letrozole salts include hydrochloride salts. In some embodiments, the drug, metabolite and/or prodrug is present in freebase form.

By "satisfactorily controlled" release profile is meant that the implant will exhibit an initial release profile that is not too steep (fast), which would otherwise lead to plasma levels that are too high with concomitant toxic side effects, and an initial release profile that is not too flat (slow), which would lead to plasma levels that are below therapeutic concentrations. An implant exhibiting a satisfactorily controlled initial release profile will release 0.5 to 20% wt., 1 to 12% wt. or 2 to 8% wt of its charge of drug within 24 hours after being placed in an aqueous environment (liquid or subject). It will release no more than 20% wt., no more than 12% wt or no more than 8% wt of its charge of drug within 24 hours after being placed in an aqueous environment. It will release at least 0.5% wt., at least 2% wt. or at least 3% wt of its charge of drug within 24 hours after being placed in an aqueous environment.

The injectable composition comprises at least a polymer, a solvent and a drug, wherein the composition has a viscosity within a specified range, the polymer has an intrinsic viscosity within a specified range, the drug has a water solubility at or below a maximum specified value, the polymer has a specified composition, and the solvent has a dipole moment and dielectric constant within specified ranges.

The polymer or polymer matrix is preferably a biocompatible and biodegradable polymer matrix. In order not to cause any severe damage to the body following administration, the preferred polymers are biocompatible, non-toxic for the human body, not carcinogenic, and do not induce significant tissue inflammation. The polymers are preferably biodegradable in order to allow natural degradation by body processes, so that they are readily disposable and do not accumulate in the body. In selecting the appropriate grade of PLGA copolymer, the time required for degradation of PLGA is related to the monomer ratio used in production: the higher the content of glycolide units, the lower the time required for degradation. In addition, polymers that are end-capped with esters (as opposed to the free carboxylic acid) demonstrate longer degradation half-lives. The preferred polymers are selected from end-capped terminal carboxylic poly-lactide and poly-glycolic acid copolymers mixed in a ratio from 48:52 to 100:0, with an inherent or intrinsic viscosity preferably in the range of 0.16-0.60 dl/g, and more preferably between 0.20-0.50 dl/g as measured in chloroform at 25° C. at a concentration of 0.1% wt/v with a Ubbelohde size 0c glass capillary viscometer (RESOMER® grades) or as measured in chloroform at 30° C. and at a concentration of 0.5% wt/v with a size 25 Cannon-Fenske glass capillary viscometer (LAKESHORE MATERIALS™ grades). The concentration of the polymeric component in the compositions of the invention is preferably in the range of about 20-50%, (expressed as the percentage of polymer weight based on total polymeric solution component) and more preferably in the range of about 25 to about 40%. Suitable grades of PLGA copolymers as described herein (according to molecular weight, intrinsic viscosity and/or molar ratio of lactic acid monomer to glycolic acid monomer) are end-capped (such as with an ester group, e.g. lauryl ester, methyl ester) are available from EVONIK® (Essen, Germany), Boehringer Ingelheim (Ingelheim am Rhein, Germany), ALKERMES (Dublin, Ireland) or SIGMA ALDRICH (ST. Louis, Mo.) and are marketed under the tradenames RESOMER®, LAKESHORE BIOMATERIALS™, or MEDISORB®. As the composition of some grades of end-capped PLGA is proprietary, the identity of the ester end-cap is not publicly available. Nonetheless, the performance properties of the grades of PLGA copolymer described herein are known and are used to characterize the material.

As used herein, the term intrinsic viscosity or inherent viscosity ($\eta_{inh}$) of the polymer is defined as the ratio of the natural logarithm of the relative viscosity, $\eta_r$, to the mass concentration of the polymer, c, i.e.:

$$\eta_{inh} = (\ln \eta_r)/c$$

and the relative viscosity ($\eta_r$) is the ratio of the viscosity of the solution $\eta$ to the viscosity of the solvent $\eta_s$, i.e.

$$\eta_r = \eta/\eta_s$$

If not otherwise specified, the intrinsic viscosity values throughout the present specification are to be understood as measured at 25° C. in chloroform at a concentration of 0.1%. The value of intrinsic viscosity is considered in the present specification, as commonly accepted in the art, as an indirect indicator of the polymer molecular weight. In this way, a reduction in the intrinsic viscosity of a polymer, measured at a given concentration in a certain solvent, with same monomer composition and terminal end groups, is an indication of a reduction in the polymer molecular weight (IUPAC. Basic definitions of terms relating to polymers; *Pure Appl. Chem.* (1974) 40, 477-491).

Suitable solvents are non-toxic, biocompatible and appropriate for parenteral injection. Solvents susceptible of causing toxicity should not be used for the injection of any material into any living body. Preferably, solvents are biocompatible in order not to cause severe tissue irritation or necrosis at the injection site. Therefore, the solvent is preferably classified as class III, according to ICH Guidelines. For the formation of the in-situ implant, the solvent should preferably diffuse quickly from the polymeric solution towards surrounding tissues when is exposed to physiological fluids. Solvent diffusion should also lead to the formation of a polymer precipitate that retains the active ingredient, effectively controlling the release of the active ingredient for at least 14 days have been achieved in certain cases up to now. Consequently, the solvent is preferably water miscible, and more preferably showing certain polarity characteristics. In this term, polarity is considered as a function of three parameters: water miscibility, dipole moment and dielectric constant. The solvent is preferably a polar aprotic solvent with a high solubility in water, having a dipole moment in the range of 3.7-4.5 D at 25° C., and a dielectric constant in the range of 30-50 at 25° C. Suitable solvents include DMSO (dimethylsulfoxide), N-methyl-pyrrolidone (NMP) and PEG (poly(ethylene glycol), e.g. MW ~200 or ~300). In some embodiments, the injectable composition comprises a combination or two or three of these solvent.

In some embodiments, the drug is completely dissolved, partially dissolved or completely undissolved in the solvent used to form the polymeric solution. Solubility of the drug in DMSO is not a critical parameter, as the composition described can effectively control drug diffusion when the drug is either dissolved or suspended in solid form in the ready-to-inject liquid composition. In some embodiments, ≤5%, ≤10%, ≤20%, ≤30%, ≤40%, ≤50%, ≤60%, ≤70%, ≤80%, ≤90%, ≤95% or ≤99% wt of the drug is dissolved in the solvent or polymeric solution to form the injectable composition. In some embodiments, ≥1%, ≥5%, ≥10%, ≥20%, ≥30%, ≥40%, ≥50%, ≥60%, ≥70% or up to about 80% wt. of the drug is dissolved in the solvent or polymeric solution to form the injectable composition.

The drug is preferably a poorly water-soluble drug with a water solubility about 2 mg/ml or less at 20° C. The poorly water soluble drug may be present in any form having the desired water solubility maximum. The advantage of this low solubility is that the initial burst of the drug when the solvent diffuses into the external aqueous medium, following placement therein, is greatly reduced. Suitable biologically active agents (drugs) include substances capable of producing a biological effect locally or either systemically, and include, for example, antipsychotics, hormones, vaccines, anti-inflammatory agents, antibacterial agents, antifungal agents, antiviral agents, analgesics, anti-parasitic agents, substances capable of regulating cellular or tissue survival or growth of function, antineoplastic agents, narcotic antagonists, and precursors or prodrugs. In preferred embodiments, the drug is selected from the group consisting of risperidone, olanzapine, letrozole or fentanyl.

One of the main factors controlling the initial release drug from the implant is the viscosity of the polymeric solution and injectable composition. The viscosity of the polymeric solution is preferably in the range of about 0.20-7.0 Pa·s, more preferably in the range of about 0.7-3.0 Pa·s, and most preferably in the range of about 0.7-2.0 Pa·s. The viscosity can be controlled primarily according to the molecular weight (the intrinsic or inherent viscosity) of the polymer and the concentration of polymer in the injectable composition.

In some embodiments, the concentration of drug in the injectable composition is generally in the range of about 4 and 40% wt or about 4 to about 25% wt, expressed as the percentage of the drug with respect to the total composition weight. More preferably, the drug content is between 7 and 35% wt, and most preferably about 13-25% wt with respect to the total composition weight.

The initial release of drug from the implant can be controlled by varying the drug/polymer mass ratio of the injectable composition. In some embodiments, this mass ratio, expressed as the percentage of the drug weight with respect to total weight of the drug plus polymer, is in the range of about 15-50% weight, more preferably about 25-50% wt, and most preferably about 33-45% wt.

Yet another factor that may contribute toward controlling the initial release of drug from the implant is the drug's particle size. Large particles provide a smaller surface area per weight thereby reducing the initial release (burst) but the release may be then delayed until the beginning of the degradation of the polymeric matrix. On the other hand, small particles evoke higher burst levels due to increased surface area and easier drug diffusion from small particles during implant hardening, followed by continuous drug release levels due to the combination of the processes of drug diffusion and implant erosion. Consequently, in a preferred embodiment of the invention a wide particle size distribution, combining large and small particle sizes in different ratios, is used in order to reduce the initial burst and still maintain a suitable constant drug release by diffusion of smaller particles during the first phase of release and gradual release of drug from the bigger particles while the polymer degrades, i.e. during the period of time (days to weeks) following the initial burst phase.

The mass ratio of the amount of solvent to the amount of risperidone (mg solvent/mg risperidone) in the injectable composition ranges may also contribute toward controlling the initial release of drug from the implant. In some embodiments, the mass ratio of the amount of solvent and the amount of drug (mg solvent/mg drug) in the injectable composition ranges from about 12:1 to about 1.5:1, about 10:1 to about 1.5:1 or about 5:1 to about 1.5:1. In some embodiments, this mass ratio is about 4.66:1, as described in the examples below.

The mass ratio of the amount of polymeric solution to the amount of drug in the injectable composition ranges may also contribute toward controlling the initial release of drug from the implant. In some embodiments, the mass ratio ranges from about 24:1 to about 1.5:1, about 12:1 to about 2:1, about 7:1 to about 2.5:1 or about 6.7:1 to about 3:1. In some embodiments, this mass ratio is about 6.66:1, as described in the examples below.

Optionally, an alkaline agent with low water solubility such as lower than 0.02 mg/ml can be included within the polymer matrix. The alkaline agent can be present in a molar ratio of from about 3/1 to 2/5, expressed as the molar ratio of drug to alkaline agent. Preferred alkaline agents are alkaline or alkaline-earth hydroxides, such as magnesium hydroxide or aluminum hydroxide. Due to the limited water solubility of the alkaline agent, the d0.5 of the particle size distribution thereof, e.g. of the magnesium hydroxide, is preferably below 10 microns.

The invention also provides an injectable composition that forms a single solid body implant in a subject to which it is administered, the composition comprising:
  a. a drug, or a metabolite or prodrug thereof, having a water solubility of less than or about 2 mg/ml; and
  b. a polymeric solution comprising a biodegradable, biocompatible polymer, which is a polymer or copolymer-based on lactic acid or a copolymer of lactic acid and glycolic acid having a monomer ratio of lactic to glycolic acid in the range from 48:52 to 100:0, wherein the polymer (or copolymer) has an inherent viscosity in the range of 0.20-0.50 dl/g, and a water-miscible solvent having a dipole moment of about 3.7-4.5 D and a dielectric constant of between 30 and 50, thereby providing the injectable composition having a viscosity in the range of about 0.50 and 4.0 Pa·s.

The invention also provides an injectable composition that forms a single solid body implant in a subject to which it is administered, the composition comprising:
  a. a drug, or a metabolite or prodrug thereof, having a water solubility of less than or about 2 mg/ml;
  b. an alkaline agent having a water solubility of about 0.02 mg/ml or less, wherein the alkaline agent is present in molar excess over the drug or wherein the drug is present in molar excess over the alkaline agent; and
  c. a polymeric solution comprising a biodegradable, biocompatible polymer, which is a polymer or copolymer-based on lactic acid or a copolymer of lactic acid and glycolic acid having a monomer ratio of lactic to glycolic acid in the range from 48:52 to 100:0, wherein the polymer (or copolymer) has an inherent viscosity in the range of 0.20-0.50 dl/g, and a water-miscible solvent having a dipole moment of about 3.7-4.5 D and a dielectric constant of between 30 and 50, thereby providing the injectable composition having a viscosity in the range of about 0.50 and 4.0 Pa·s.; wherein d. the concentration of drug in the injectable composition is in the range of about 4% to about 40% wt, expressed as the percentage of the drug with respect to the total composition weight; and e. the composition provides a satisfactorily controlled release profile throughout a dosing period of at least 21 days after administration.

The invention also provides an injectable composition that forms a single solid body implant in a subject to which it is administered, the composition comprising:

a. A drug selected from the group consisting of Olanzapine, risperidone, paliperidone, fentanyl or letrozole;

b. an alkaline agent selected from the group consisting of magnesium hydroxide and aluminum hydroxide, wherein the alkaline agent is present in molar excess over the drug or wherein the drug is present in molar excess over the alkaline agent; and c. a polymeric solution comprising a biodegradable, biocompatible PLGA copolymer of lactic acid and glycolic acid having a monomer ratio of lactic to glycolic acid in the range from 48:52 to 100:0, wherein the copolymer has an inherent viscosity in the range of 0.20-0.50 dl/g, and dimethylsulfoxide, thereby providing the injectable composition having a viscosity in the range of about 0.50 and 4.0 Pa·s.; wherein d. the concentration of drug in the injectable composition is in the range of about 4% to about 40% wt, expressed as the percentage of the drug with respect to the total composition weight; and e. the composition provides a satisfactorily controlled release profile throughout a dosing period of at least 21 days after administration.

Figure 47:
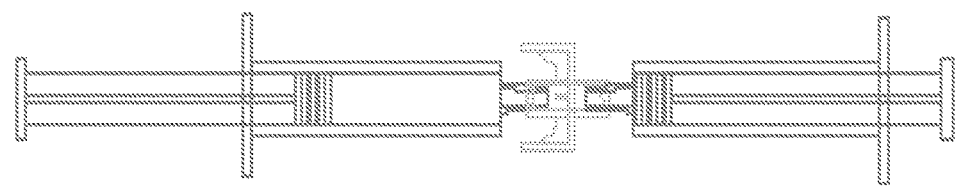
FIGS. 47 and 48. depict exemplary embodiments of syringes suitable for administering the injectable composition.
Figure 48:
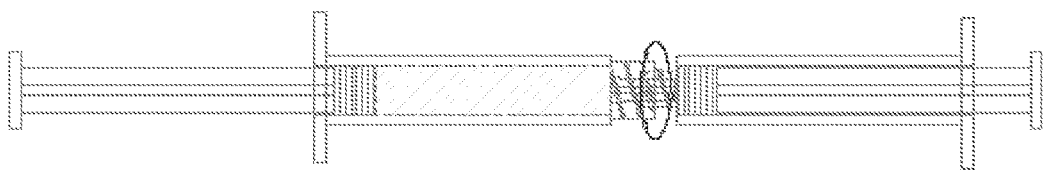

Another aspect of the invention provides a kit comprising: a first container containing a polymer in solid form, drug and, optionally, Mg(OH)$_2$ in predetermined amounts; and a second container containing a water-miscible solvent. When required, the contents of both containers are combined, for example through a connector or by using male-female syringes, and mixed each other so that the compositions according to the invention are reconstituted, for example by moving forwards and backwards the plungers of the syringes. The polymer is preferably provided in freeze-dried (lyophilized) form. Each container is independently selected at each occurrence from a syringe, vial, device and cartridge. Each container is independently at each occurrence disposable or not disposable. Illustrative preferred embodiments of the containers are depicted in FIG. 47 (syringes connected through a connector device) and in FIG. 48 (syringes connected through a direct thread)

In some embodiments, the injectable depot composition is sterile as a finished product. The biocompatible polymer can be sterilized prior to its aseptic filling process, preferably by an aseptic filling process by beta-irradiation in the range 5-25 KGy or it can be sterilized after being dissolved in a solvent to form a polymeric solution followed by filtration of the polymeric solution through a filter with a 0.22 µm pore size or less. Alternatively, the drug and/or the biocompatible polymer of the composition may be subjected to terminal sterilization processes, preferably by beta-irradiation in the range 5-25 KGy.

The polymer can be sterilized by β-irradiation. Example 15 describes an exemplary process for sterilization of the composition. The polymer and risperidone were mixed and subjected to β-irradiation in the range 10-25 KGy. Exposure to radiation caused the polymer to degrade thereby resulting in a polymer with reduced molecular weight and a corresponding polymer solution with reduced viscosity. In some embodiments, the invention provides a process for preparing an injectable composition as described herein, the process comprising: a) subjecting a PLGA polymer to a sufficient amount of β-irradiation to degrade at least a portion of the polymer thereby reducing its molecular weight; and b) dissolving the polymer in a solvent to form a polymeric solution having a desired viscosity. In some embodiments, a mixture of drug and PLGA polymer are exposed to beta-irradiation prior to addition of the solvent, which would result in formation of a sterilized injectable composition of the invention.

Embodiments of the invention include those wherein: a) the molecular weight of the polymer is greater before irradiation than it is after irradiation; b) the molecular weight of the polymer is greater than 10 KDa before irradiation; c) the molecular weight of the polymer is in the range of 10-60 KDa, 10-52 KDa or 10-43 KDa after irradiation; d) the viscosity of a polymeric solution containing polymer that has not been irradiated is greater than about 0.5 Pa·s; e) the viscosity of a polymeric solution containing polymer that has been irradiated is in the range of 0.5-7.0 Pa·s, 0.5-3.0 Pa·s or 0.7 to 2.0 Pa·s.; and/or f) the sufficient amount of radiation is at least 10, at least 15, at least 20 or at least 25 KGy.

In another preferred embodiment, in the injectable depot composition at least the drug and/or the biocompatible polymer of the composition have been submitted to terminal sterilization processes, preferably by irradiation in the range of 5-25 KGy.

The injectable composition is used to treat a disorder, disease or condition that is therapeutically responsive to a drug. The invention comprises administering to a subject in need thereof an amount of injectable composition sufficient to provide therapeutic plasma levels of drug in the subject during the period of at least 1 to 14, at least 2 to 14 or at least 3 to 14 days after administration (the dosing period). The dosing period can exceed two weeks and can be up to three weeks, four weeks, five weeks, six weeks, two months, three months, four months, five months or six months. The method can comprise one or more or plural dosing periods as part of an overall treatment period.

As used herein, the term "dosing period" refers to the period of days or weeks as measured from the initial day after administration to at least 14 days after administration. During the dosing period, the implant will provide therapeutic plasma levels of drug for at least 11 days, at least 12 days, at least 13 days, at least 14 days, at least 21 days, at least 28 days, at least 31 days or at least 36 days. The dosing period can exceed two weeks and can be up to three weeks, four weeks, five weeks, six weeks, two months, three months, four months, five months or six months. A dosing period can end after expiration of a predetermined number of days or after the plasma level of risperidone drops below therapeutic levels.

As used herein, a "treatment period" refers to the weeks, months or years during which implants of the invention are administered to a subject. A treatment period generally comprises plural dosing periods. Dosing periods can occur sequentially or in an overlapping manner during a treatment period. A treatment period will vary according to the drug administered and the disease, disorder or condition being treated and according to the dosage and administration protocols approved by the U.S.F.D.A. for each drug. For example, a first dose of injectable composition is administered and a second dose of injectable composition can be administered within one to two weeks following administration of the first dose, such that each dose will have its own corresponding dosing period, and the dosing periods would overlap.

The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a dosing period.

Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a dosing period.

The plasma concentration profile during the dosing period can exhibit one, two, or more maxima and one, two or more minima. An initial maximum can be caused by dissolution of risperidone during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to three days or one to two days of the dosing period; b) the plasma profile exhibits a maximum during the latter 11 to 13 days or 12 to 14 days of the dosing period; c) the plasma profile exhibits a maximum during the initial days of the dosing period and a maximum during the remaining days of the dosing period; or d) the plasma profile is substantially level (within ±20%, ±15%, ±10% or ±5% of the average or mean) during the dosing period.

The implant of the invention can provide substantially improved plasma levels of drug during the initial one to three days after administration when compared to another injectable formulation (not according to the invention) containing the same drug when administered on an equivalent dose basis.

In humans, the average plasma concentration of risperidone can range from about 3-200, about 5-80, or about 10-60 ng/ml when an amount of injectable composition equivalent to a dose of about 25-150, about 37.5-125, or about 50-100 mg of risperidone is administered. The average Cmin during the dosing period is in the range of about 1-80, 5-50, or about 5-40 ng/ml when an amount of injectable composition equivalent to a dose of about 25-150, about 37.5-125, or about 50-100 mg, respectively, of risperidone is administered. The average Cmax during the dosing period is in the range of about 8-300, 10-150, or 10-120 ng/ml when an amount of injectable composition equivalent to a dose of 25-150, 37.5-125, or 50-100 mg, respectively, of risperidone is administered. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

As used herein, whenever the plasma concentration of a drug is mentioned, such plasma concentration includes within it the sum total of the plasma concentration of the drug and its active metabolite(s). For example, whenever the plasma concentration of risperidone is mentioned, such plasma concentration includes within it the sum total of the plasma concentrations of risperidone and its active metabolite(s), such as 9-OH-risperidone (paliperidone).

As used herein the term, "initial burst" or "initial release" refers to the addition of the plasma levels of drug plus active metabolite(s), which addition is also called "the active moiety" throughout the present specification, from the moment of injection/administration of the injectable composition to a subject in need thereof until completion of the third day after the administration. For example, the drug can be risperidone and its metabolite can be paliperidone. In some embodiments, the initial period of release is within three days, within two days, within one day or within twelve hours after administration.

The following examples illustrate the invention and should not be considered as defining the full scope thereof.

Comparative Example 1: Implantable Composition Including a Drug Having a Water Solubility >2 mg/mL (Example not According to the Invention)

In the present example, the composition of the implantable formulation was as follows:

| Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|
| | | | | Drug | Polymer | Solvent | |
| Rivastigmine base | 50:50 | 0.40 | DMSO | 50 | 100 | 233.2 | 1.12 |
| Rivastigmine tartrate | 50:50 | 0.40 | DMSO | 50 | 100 | 233.2 | 1.12 |
| Bemiparin | 50:50 | 0.40 | DMSO | 50 | 200 | 466.6 | 1.12 |

The implantable formulations were prepared by completely dissolving the polymer in the solvent, thereby forming the so-called "polymeric solution", and subsequently adding the drug to the polymeric solution.

In Vitro Release Profile:

The drug released from each formulation of this example was evaluated according to the following procedure: The amount of formulation corresponding to 25 mg of drug was injected from prefilled syringes into flasks having a pre-warmed release medium by using a 21 G needle. The release-medium was 250 ml phosphate buffer, pH=7.4. The flasks were then placed into an oven at 37° C. and kept under horizontal shaking at 50 rpm. At previously scheduled time points (2 h, 1 d, and periodically up to 14 days), 5 ml of release medium was collected and replaced with fresh buffer and the amount of drug present in the sample was determined by UV spectrophotometry for rivastigmine base and tartrate, and nephelometry in the case of bemiparin. The profile of drug released from the implants of this example is shown in FIG. 1. The results are expressed as % drug released from implants as a function of time.

As depicted in FIG. 1, the release of rivastigmine tartrate and bemiparin during the first 24 hours is completely uncontrollable, being higher than 70% of the injected amount. In the case of rivastigmine base, the release was substantially lower, however it was also quite high during the first 24 hours, close to 15% of the injected amount and close to 35% in the first 48 hours and 80% after 5 days, therefore producing a high drug release by diffusion process and a consequent incapacity of the formulation to control the release of the drugs.

In Vivo Plasma Levels after Intramuscular Administration to New Zealand Rabbit:

The rivastigmine formulations of this example were injected intramuscularly to New Zealand White rabbits weighing an average of 3 kg. The amount injected corresponded to a dose of 30 mg rivastigmine and the formulation was placed intramuscularly in the left hind leg using a syringe with a 20 G needle. The total number of rabbits per formulation was 3. After injection, plasma levels were obtained at 0, 4 h, 1 d, 2 d, 4 d and 7 d.

Figure 2:
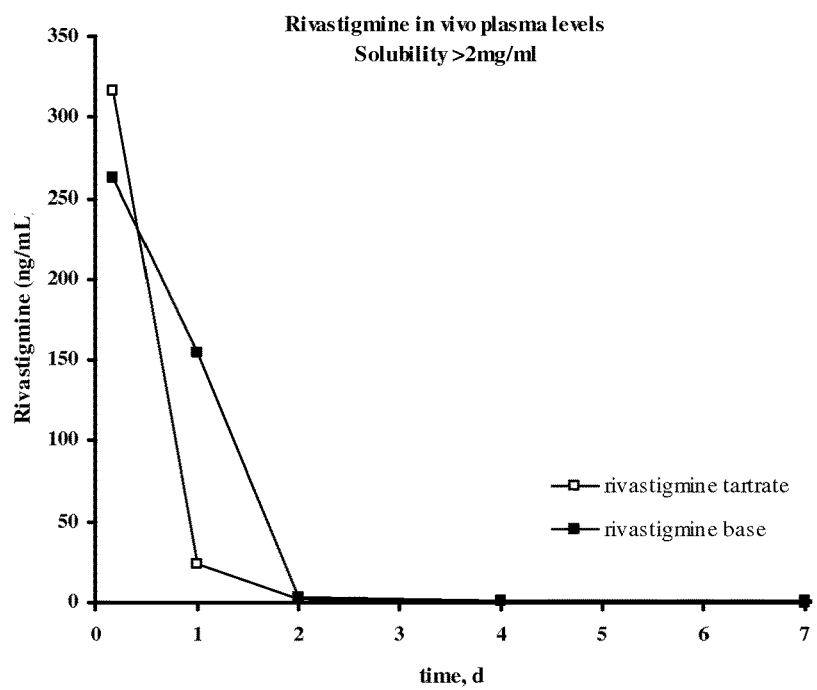
FIG. 2 depicts the plasma levels profile of Rivastigmine in New Zealand rabbits provided by implants prepared according to Comparative Example 1. Results are expressed as the concentration of Rivastigmine as a function of time.

The kinetics of the plasma levels corresponding to the rivastigmine was evaluated. The profile of the plasma levels of the rivastigmine is shown in FIG. 2. As it can be observed in this Figure, the injection of an amount of formulation equivalent to 30 mg rivastigmine to New Zealand White rabbits resulted in very high initial plasma levels followed by a rapid decrease, with no significant plasma levels from day 2 onwards.

These results are in accordance with in vitro findings, which demonstrates the rather poor control on the initial drug release achieved when drugs with solubility >2 mg/ml are used in the formulations of the invention.

Example 1: Implantable Composition Including a Drug with Water Solubility <2 mg/mL In the present example, the composition of the implantable formulation was as follows:

| Drug | Polymer lactic/glycolic ratio | Polymer Inherent Viscosity (dL/g) | Solvent | Component Amount (mg) | | | Polymer Solution Viscosity (Pa · s) |
| --- | --- | --- | --- | --- | --- | --- | --- |
| | | | | Drug | Polymer | Solvent | |
| Fentanyl | 50:50 | 0.40 | DMSO | 25 | 150 | 350 | 1.12 |
| Olanzapine | 50:50 | 0.40 | DMSO | 25 | 50 | 116.6 | 1.12 |
| Risperidone (in vitro profile) | 50:50 | 0.40 | DMSO | 25 | 50 | 116.6 | 1.12 |
| Risperidone (in vivo profile) | 50:50 | 0.40 | DMSO | 25 | 100 | 233.2 | 1.12 |
| Letrozole (in vitro profile) | 50:50 | 0.43 | DMSO | 25 | 50 | 116.6 | 1.62 |
| Letrozole (in vivo profile) | 50:50 | 0.43 | DMSO | 25 | 30 | 70 | 1.62 |

The implantable formulations were prepared by completely dissolving the polymer in the solvent and subsequently adding the drug in said polymeric solution.

Figure 3:
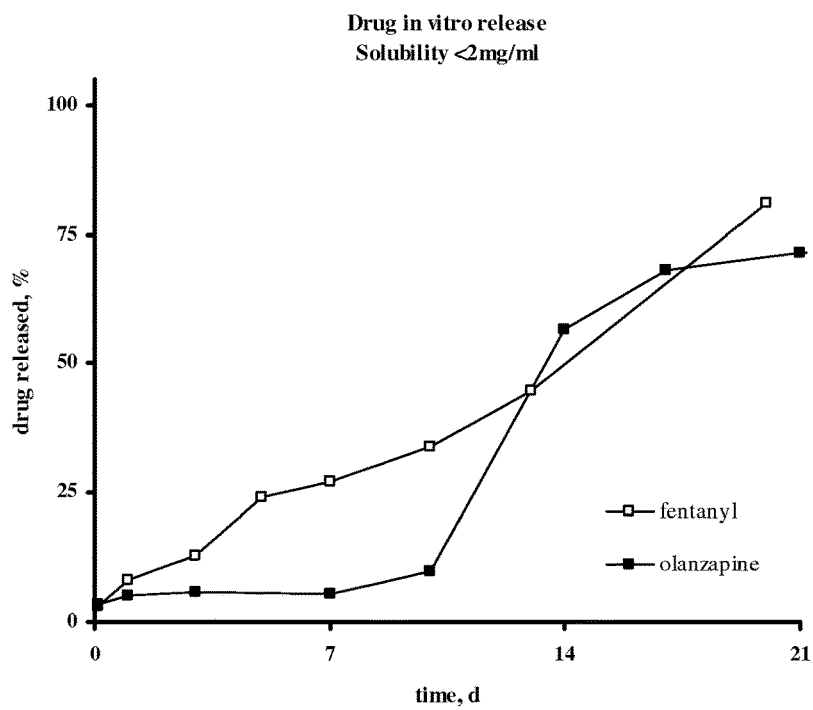
FIG. 3 depicts the release profile of Fentanyl and Olanzapine from implants prepared according to Example 1. Results are expressed as % drug released from implants as a function of time.

In Vitro Release Profile:

The drug released from each formulation of this example was evaluated according to the following procedure depending on the formulated drug: The amount of formulation corresponding to 9, 10, 25 or 3 mg of fentanyl, olanzapine, risperidone or letrozole was injected from prefilled syringes into flasks having a pre-warmed release medium by using a 21 G needle. The release medium was phosphate buffer pH=7.4 (100 ml for fentanyl and 250 ml for the remaining drugs). The flasks were then placed into an oven at 37° C. and kept under horizontal shaking at 50 rpm. At previously scheduled time points (2 h, 1 d, and periodically up to 21, 42 or 58 days), 5 ml of release medium was collected and replaced with fresh buffer and the amount of drug present in the sample was determined by UV spectrophotometry (fentanyl, olanzapine, risperidone) or HPLC-FLD (letrozole). The profile of drug released from the implants of this example is shown in FIG. 3 (fentanyl, olanzapine) and FIG. 4 (risperidone, letrozole). The results are expressed as % drug released from implants as a function of time.

Figure 4:
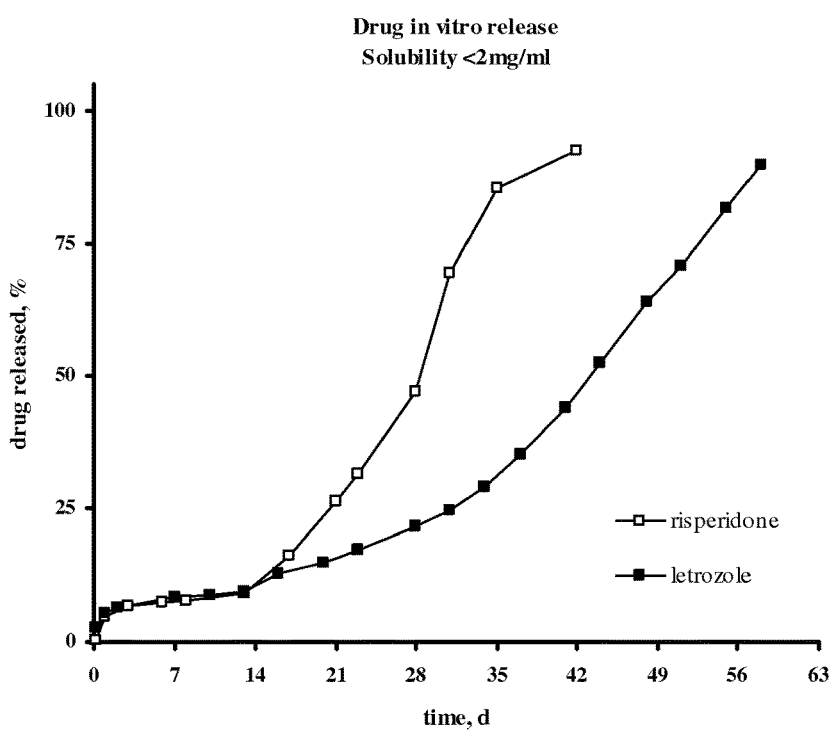
FIG. 4 depicts the release profile of Risperidone and Letrozole from implants prepared according to Example 1. Results are expressed as % drug released from implants as a function of time.

As depicted in FIGS. 3 and 4, the release of the four drugs was controlled to a different extent depending on the drug, but in all cases a certain control was obtained at least during 21 days. None of the drugs showed a high initial burst release, such release being less than 10% during the first 24 hours and less than 15% during the first 3 days in all the cases.

In Vivo Plasma Levels after Intramuscular Administration to New Zealand Rabbit:

The risperidone and letrozole formulations of this example were injected intramuscularly to New Zealand White rabbits weighing an average of 3 kg. The amount injected corresponded to a dose of 15 mg risperidone or 5.4 mg letrozole, and the formulation was placed intramuscularly in the left hind leg using a syringe with a 20 G needle. The total number of rabbits per composition was 3. After injection, plasma levels were obtained at 0, 4 h, 1 d, 2 d, 3 d, 5 d, 7 d, 10, 14 d and periodically up to 35 d and 56 d, respectively.

Figure 5:
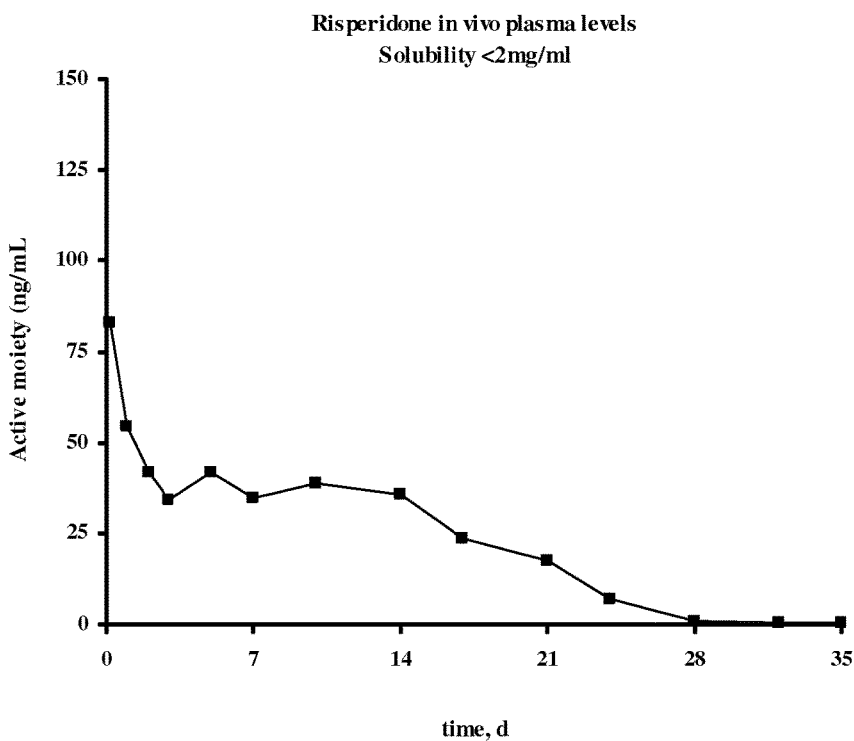
FIG. 5 depicts the plasma level profile of Risperidone in New Zealand rabbits provided by implants prepared according to Example 1. Results are expressed as the sum of the concentration of Risperidone and its active metabolite 9-hydroxide-risperidone as a function of time.
Figure 6:
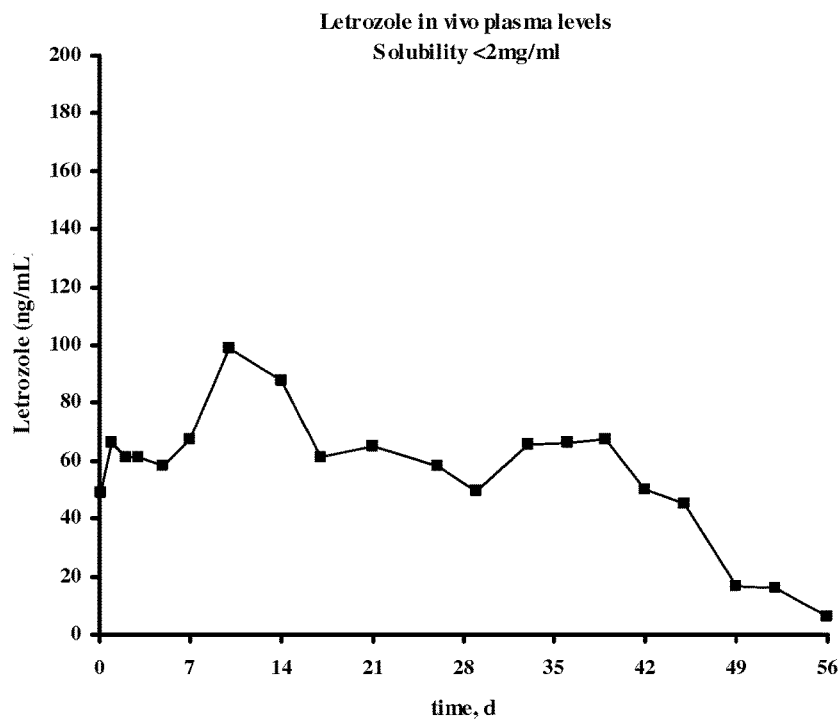
FIG. 6 depicts the plasma level profile of Letrozole in New Zealand rabbits provided by implants prepared according to Example 1. Results are expressed as the concentration of Letrozole as a function of time.

The kinetics of the drug plasma levels corresponding to the each composition was evaluated. The profile of the plasma levels of the risperidone (active moiety, corresponding to risperidone plus its pharmacologically equivalent metabolite 9-OH-risperidone) and letrozole is shown in FIG. 5 and FIG. 6, respectively. As it can be observed in these Figures, the injection of an amount of formulation equivalent to 15 mg risperidone or 5.4 mg letrozole to New Zealand White rabbits resulted in controlled initial plasma levels, conferring to the compositions a duration of at least 21 and 49 days, respectively, with constant levels until the drug is completely released when plasma levels decline.

Example 2: Implantable Composition Including a Drug with Water Solubility <2 mg/mL (Continuation)

In the present example, the composition of the implantable formulation was as follows:

| Drug | Polymer lactic/glycolic ratio | Polymer Inherent Viscosity (dL/g) | Solvent | Component Amount (mg) | | | Polymer Solution Viscosity (Pa·s) |
|---|---|---|---|---|---|---|---|
| | | | | Drug | Polymer | Solvent | |
| Fentanyl | 50:50 | 0.40 | DMSO | 25 | 100 | 250 | 6.77 |
| Olanzapine | 50:50 | 0.40 | DMSO | 50 | 50 | 100 | 1.85 |

In Vivo Plasma Levels after Intramuscular Administration to New Zealand Rabbit:

The formulations of this example were intramuscularly injected to New Zealand White rabbits weighing an average of 3 kg. The amount injected corresponded to a dose of 4.2 mg fentanyl or 46.2 mg olanzapine, and the composition was intramuscularly placed in the left hind leg using a syringe with a 20 G needle. The total number of rabbits per formulation was 3. After injection, plasma levels were obtained at 0, 4 h, 1 d, 2 d, and periodically up to 14 d and 36 d, respectively.

Figure 7:
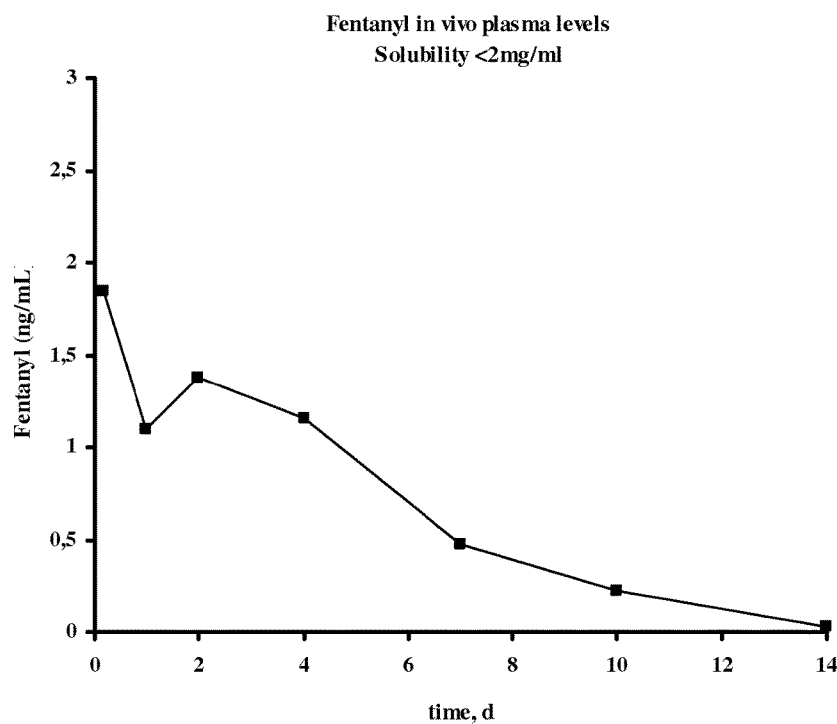
FIG. 7 depicts the plasma level profile of Fentanyl in New Zealand rabbits provided by implants prepared according to Example 2. Results are expressed as the concentration of Fentanyl as a function of time.
Figure 8:
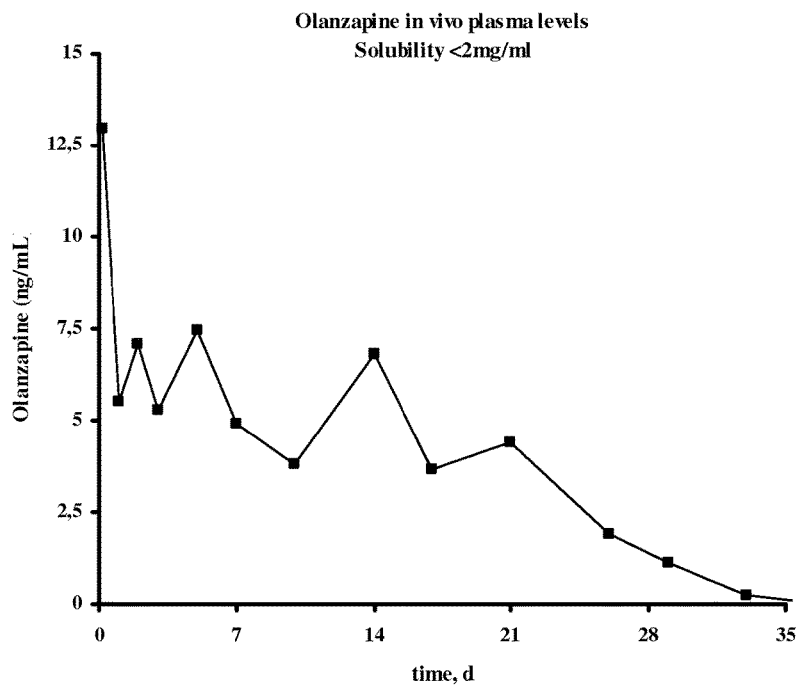
FIG. 8 depicts the plasma level profile of Olanzapine in New Zealand rabbits provided by implants prepared according to Example 2. Results are expressed as the concentration of Olanzapine as a function of time.

The kinetics of the drug plasma levels corresponding to the each composition was evaluated. The profile of the plasma levels of the fentanyl and olanzapine is shown in FIG. 7 and FIG. 8, respectively. As it can be observed in these Figures, the injection of an amount of composition equivalent to 4.2 mg fentanyl or 46.2 mg olanzapine to New Zealand White rabbits resulted in controlled initial plasma levels, conferring to the compositions a duration of at least 14 and 28 days, respectively, with constant levels, particularly in the case of olanzapine, until the drug is almost completely released when plasma levels decline.

The results of this example, together with Example 1, show that drugs having a water solubility lower than 2 mg/mL can be satisfactorily used in the implantable formulations of the invention.

Example 3: Different Inherent Viscosities of the Polymer for the Drug Fentanyl

In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa·s) |
|---|---|---|---|---|---|---|---|---|
| | | | | | Drug | Polymer | Solvent | |
| A | Fentanyl | 50:50 | 0.40 | DMSO | 25 | 75 | 175 | 1.12 |
| B | Fentanyl | 50:50 | 0.40 | DMSO | 25 | 100 | 150 | 6.77 |
| C | Fentanyl | 75:25 | 0.20 | DMSO | 25 | 200 | 300 | 0.43 |
| D | Fentanyl | 75:25 | 0.20 | DMSO | 25 | 125 | 125 | 1.95 |

The implantable formulations were prepared by completely dissolving the polymer in the solvent and subsequently adding the drug in said polymeric solution.

Figure 9:
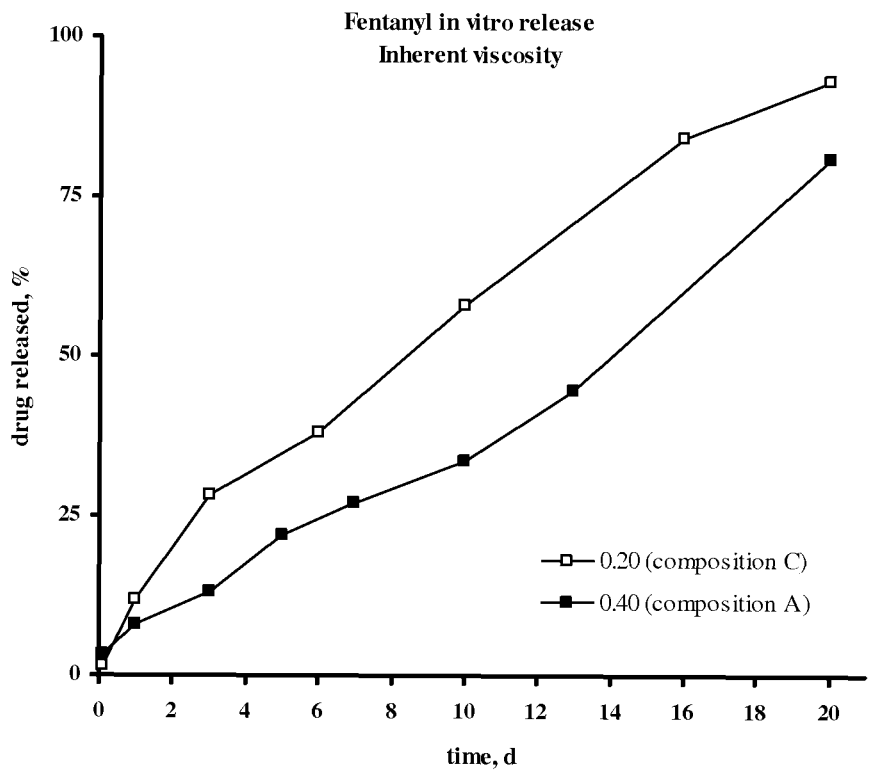
FIG. 9 depicts the release profile of Fentanyl from implants prepared according to Example 3. Results are expressed as % Fentanyl released from implants as a function of time.

In Vitro Release Profile:

The drug released from formulations A and C of this example was evaluated according to the following procedure: The amount of formulation corresponding to 9 mg of fentanyl was injected from prefilled syringes into flasks having a pre-warmed release medium by using a 21 G needle. The release medium was 100 ml phosphate buffer pH=7.4. The flasks were then placed into an oven at 37° C. and kept under horizontal shaking at 50 rpm. At previously scheduled time points (2 h, 1 d, and periodically up to 20 d), 5 ml of release medium was collected and replaced with fresh buffer and the amount of fentanyl present in the sample was determined by UV spectrophotometry. The profile of fentanyl released from the implants of this example is shown in FIG. 9. The results are expressed as % drug released from the implants as a function of time.

As depicted in FIG. 9, the release of the fentanyl is controlled better when 0.40 dL/g inherent viscosity polymer (composition A) is used instead of 0.20 dL/g (composition C). The higher inherent viscosity polymer is capable of controlling the initial burst during first 24 hours, such burst being lower than 10% in the case of 0.40 dL/g, whereas it is above 10% in the case of 0.20 dL/g polymer. After 3 days, in the case of 0.20 dL/g inherent viscosity the release is close to 30%, and close to 60% after 10 days, whereas in the case of 0.40 dL/g viscosity the release is below 15% and 30% after 3 and 10 days respectively.

In Vivo Plasma Levels after Intramuscular Administration to New Zealand Rabbit:

The fentanyl formulations of this example were injected intramuscularly to New Zealand White rabbits weighing an average of 3 kg. The amount injected corresponded to a dose of 4.2 mg fentanyl, and the formulation was placed intramuscularly in the left hind leg using a syringe with a 20 G needle. The total number of rabbits per composition was 3. After injection, plasma levels were obtained at 0, 4 h, 1 d, 2 d, 4 d, 7 d, 10 d and 14 d.

Figure 10:
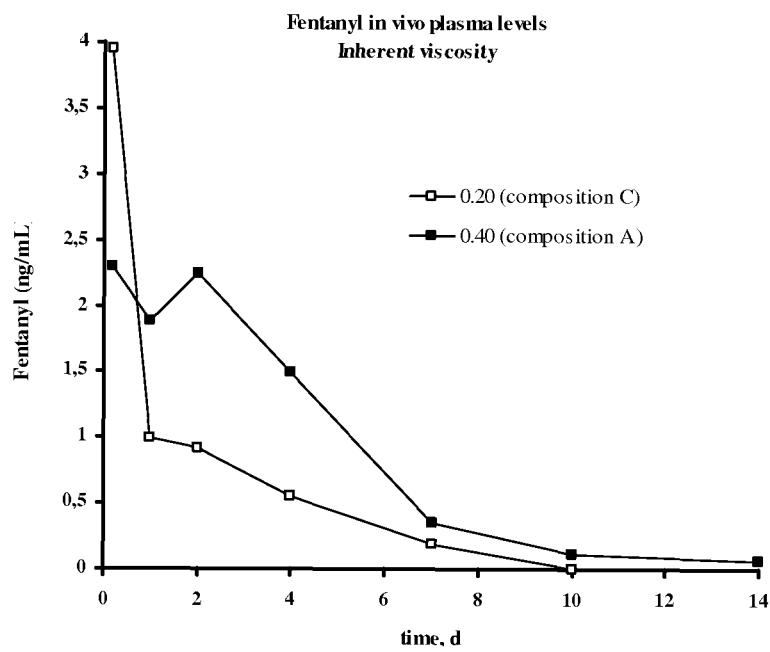
FIG. 10 depicts the plasma level profile of Fentanyl in New Zealand rabbits provided by implants prepared according to Example 3. Results are expressed as the concentration of Fentanyl as a function of time.
Figure 11:
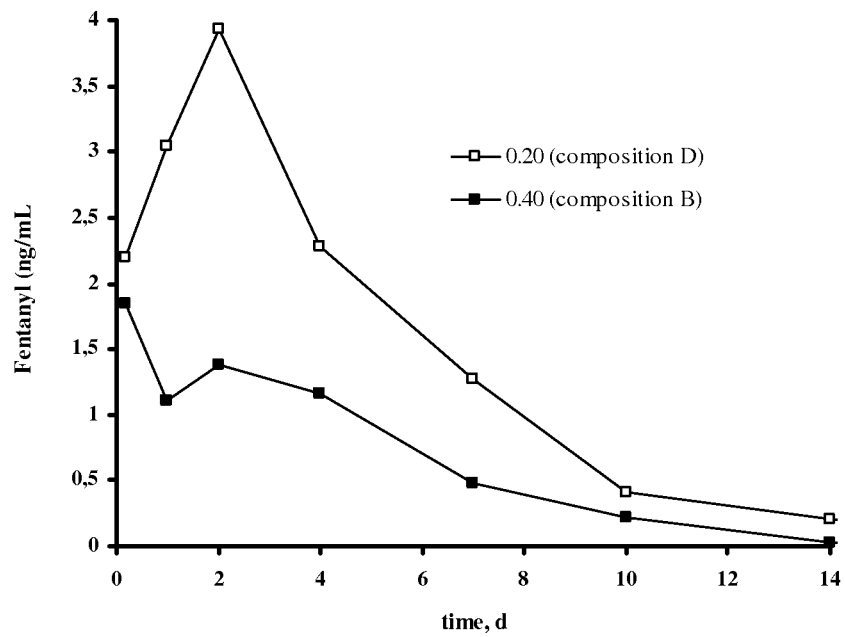
FIG. 11 depicts the plasma level profile of Fentanyl in New Zealand rabbits provided by implants prepared according to Example 3. Results are expressed as the concentration of Fentanyl as a function of time.

The kinetics of fentanyl plasma levels corresponding to the each composition was evaluated. The profile of the plasma levels of fentanyl is shown in FIGS. 10 and 11. As depicted in these figures, the injection of an amount of formulation equivalent to 4.2 mg fentanyl to New Zealand White rabbits resulted in better controlled initial plasma levels (first 3 days) when a polymer with an inherent viscosity of 0.40 dL/g (compositions A and B) instead of 0.20 dL/g (compositions C and D) was used.

Example 4: Different Inherent Viscosities of the Polymer for the Drug Olanzapine In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa · s) |
| --- | --- | --- | --- | --- | --- | --- | --- | --- |
| | | | | | Drug | Polymer | Solvent | |
| A | Olanzapine | 50:50 | 0.43 | DMSO | 25 | 50 | 116.6 | 1.62 |
| B | Olanzapine | 50:50 | 0.43 | DMSO | 25 | 33.3 | 66.7 | 3.16 |
| C | Olanzapine | 75:25 | 0.20 | DMSO | 25 | 66.6 | 100 | 0.43 |
| D | Olanzapine | 75:25 | 0.38 | DMSO | 25 | 50 | 116.6 | 0.66 |
| E | Olanzapine | 100:0 | 0.30 | DMSO | 25 | 25 | 50 | 0.46 |

The implantable formulations were prepared by completely dissolving the polymer in the solvent and subsequently adding the drug in said polymeric solution.

Figure 12:
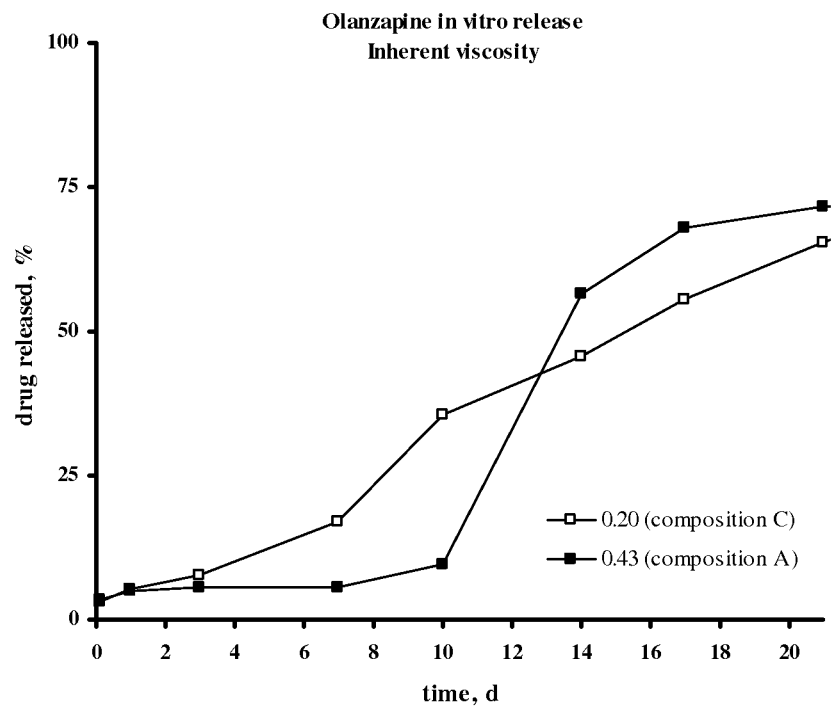
FIGS. 12 and 13 depict the release profile of Olanzapine from implants prepared according to Example 4. Results are expressed as % Olanzapine released from implants as a function of time.
Figure 13:
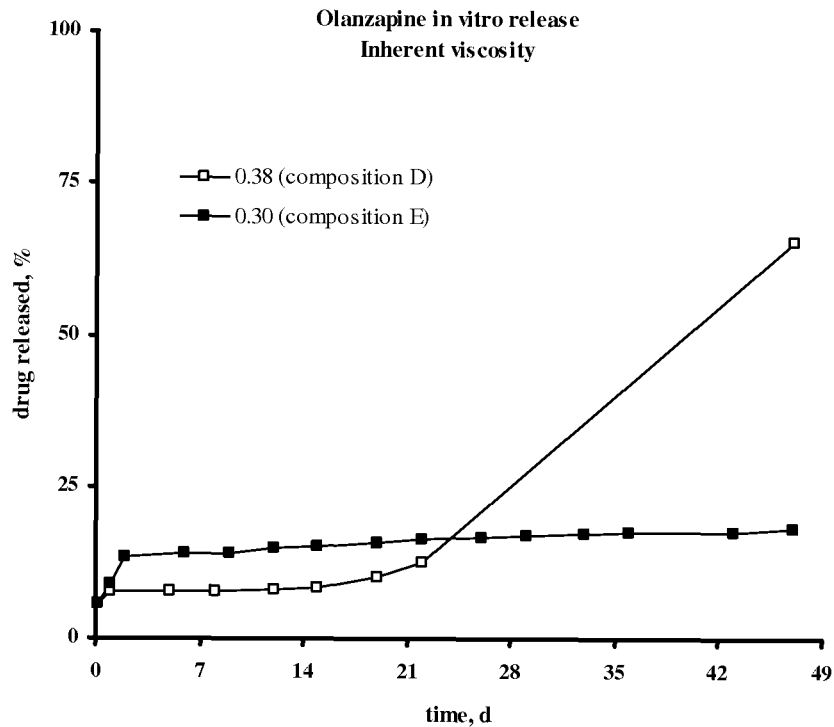

In Vitro Release Profile:

The drug released from composition A, C, D and E of this example was evaluated according to the following procedure. The amount of formulation corresponding to 10 mg of olanzapine was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 21 d or 49 d), 5 ml of release medium was collected and replaced with fresh buffer and the amount of olanzapine present in the sample was determined by UV spectrophotometry. The profile of olanzapine released from the implants of this example is shown in FIGS. 12 and 13. The results are expressed as % drug released from implants as a function of time.

As depicted in FIG. 12, the release of the olanzapine is not satisfactorily controlled when a 0.20 dL/g inherent viscosity formulation (formulation C) is used instead of 0.43 dL/g (formulation A), the latter showing an overall faster drug release in spite of the fact that the former formulation comprises a 75:25 lactic/glycolic polymer with a degradation time slower than a 50:50 one, probably due to a high diffusion process resulting in the shown incapability to retain the drug. On the other hand, the formulation with 0.43 dL/g inherent viscosity showed a controlled drug release until the polymer started to degrade (around 10 days). FIG. 13 shows how polymers with inherent viscosity of 0.30 and 0.38 dL/g are also capable to satisfactorily control the initial olanzapine release until at least the time when the polymer begins to degrade, namely around 21 days for 75:25 lactic/glycolic polymer (formulation D) and longer than 49 days for 100:0 lactic/glycolic polymer (formulation E).

In Vivo Plasma Levels after Intramuscular Administration to New Zealand Rabbit:

The olanzapine formulations B and D of this example were injected intramuscularly to New Zealand White rabbits weighing an average of 3 kg. The amount injected corresponded to a dose of 46.3 mg olanzapine, and the composition was placed intramuscularly in the left hind leg using a syringe with a 20 G needle. The total number of rabbits per composition was 3. After injection, plasma levels were obtained at 0, 4 h, 1 d, 2 d, 4 d, 7 d, 10 d and periodically up to 56 days.

Figure 14:
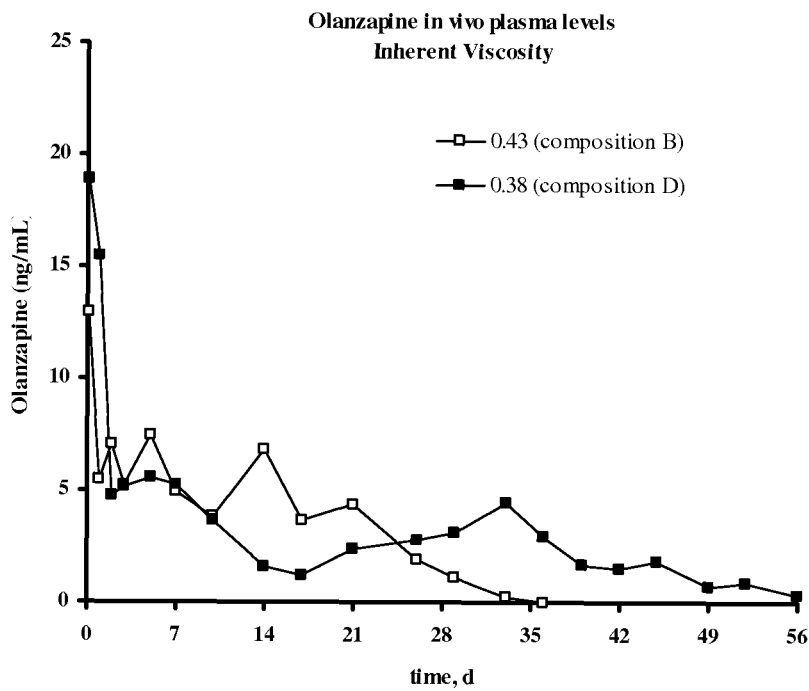
FIG. 14 depicts the plasma level profile of Olanzapine in New Zealand rabbits provided by implants prepared according to Example 4. Results are expressed as the concentration of Olanzapine as a function of time.

The kinetics of olanzapine plasma levels corresponding to the each composition was evaluated. The profile of the plasma levels of olanzapine is shown in FIG. 14. As depicted in this figure, the injection of an amount of formulation equivalent to 46.2 mg olanzapine to New Zealand White rabbits resulted in constant and controlled initial plasma levels (first 3 days) when a polymer with an inherent viscosity of 0.38 and 0.43 dL/g was used, with duration periods of 49 and 28 days respectively.

Example 5: Different Inherent Viscosities of the Polymer for the Drug Risperidone In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|---|
| | | | | | Drug | Polymer | Solvent | |
| A | Risperidone | 50:50 | 0.22 | DMSO | 25 | 116.3 | 215.9 | 0.32 |
| B | Risperidone | 50:50 | 0.22 | DMSO | 25 | 166.1 | 166.1 | 3.18 |
| C | Risperidone | 50:50 | 0.40 | DMSO | 25 | 100 | 233.3 | 1.12 |
| D | Risperidone | 75:25 | 0.20 | DMSO | 25 | 100 | 150 | 0.43 |
| E | Risperidone | 75:25 | 0.38 | DMSO | 25 | 50 | 116.6 | 0.66 |
| F | Risperidone | 100:0 | 0.30 | DMSO | 25 | 50 | 116.6 | 0.26 |

The implantable formulations were prepared by completely dissolving the polymer in the solvent and subsequently adding the drug in said polymeric solution.

Figure 15:
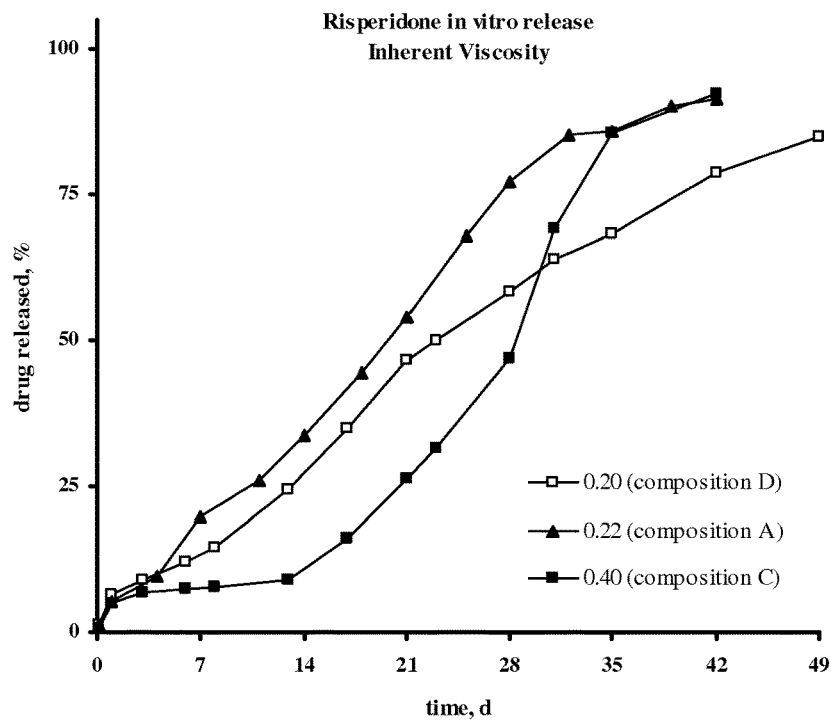
FIG. 15 depicts the release profile of Risperidone from implants prepared according to Example 5. Results are expressed as % Risperidone released from implants as a function of time.

In Vitro Release Profile:

The drug released from formulations A, C, and D of this example was evaluated according to the following procedure: The amount of formulation corresponding to 25 mg of risperidone was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 49 d), 5 ml of release medium was collected and replaced with fresh buffer and the amount of risperidone present in the sample was determined by UV spectrophotometry. The profile of risperidone released from the implants of this example is shown in FIG. 15. The results are expressed as % drug released from implants as a function of time.

As depicted in FIG. 15, the release of the risperidone is not satisfactorily controlled when polymers having 0.20 and 0.22 dL/g inherent viscosity values (Formulations D and A, respectively) were used instead of 0.40 dL/g (Formulation C), the latter formulations showing faster drug releases in spite of the fact that the 75:25 lactic/glycolic polymer (composition D) has a degradation time slower than a 50:50 polymer. These low inherent viscosity polymers demonstrate their inability for an adequate control of the drug release, probably due to the fact that they evoke high drug diffusion processes. Once again, 0.40 dL/g inherent viscosity polymers show a well-controlled drug release until the polymer starts to degrade (around 14 days).

In Vivo Plasma Levels after Intramuscular Administration to New Zealand Rabbit:

The risperidone compositions B, C, D, E and F of this example were injected intramuscularly to New Zealand White rabbits weighing an average of 3 kg. The amount injected corresponded to a dose of 15 mg risperidone, and the composition was placed intramuscularly in the left hind leg using a syringe with a 20 G needle. The total number of rabbits per composition was 3. After injection, plasma levels were obtained at 0, 4 h, 1 d, 2 d, 4 d, 7 d, 10 d and periodically up to 28 days.

Figure 16:
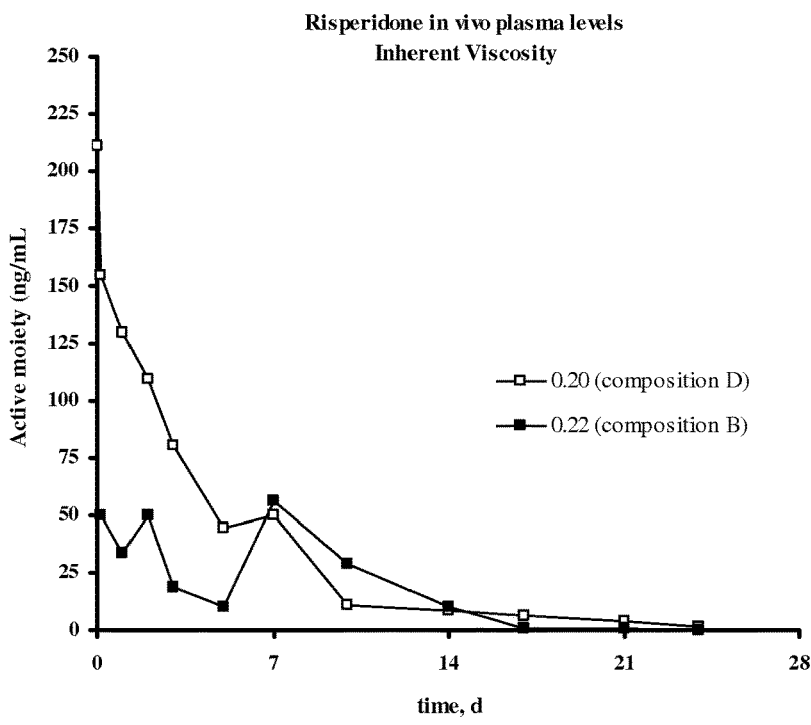
FIG. 16 depicts the plasma level profile of Risperidone in New Zealand rabbits provided by implants prepared according to Example 5. Results are expressed as the sum of the concentrations of Risperidone and its active metabolite 9-hydroxide-risperidone as a function of time.
Figure 17:
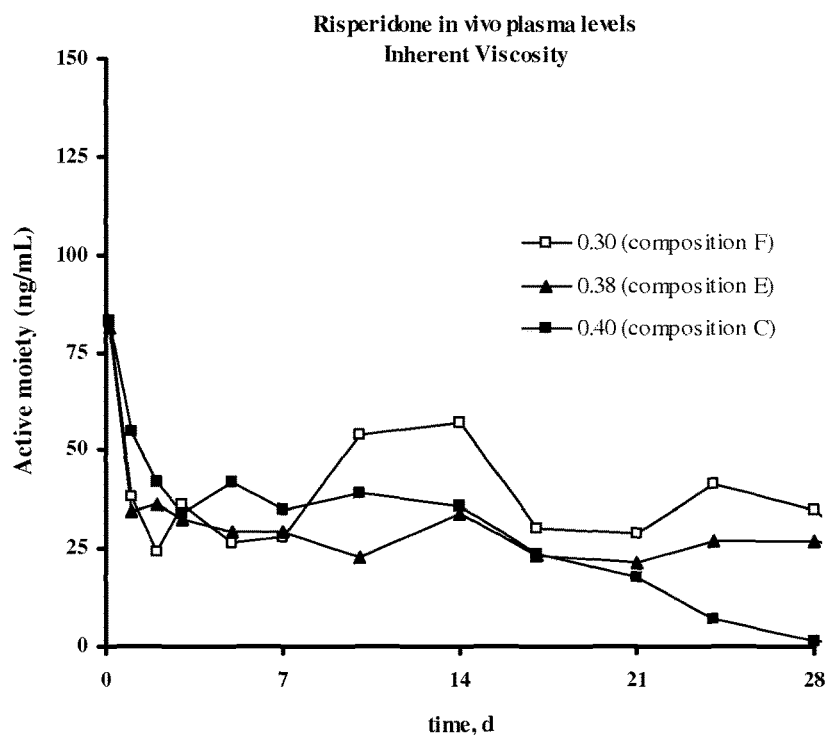
FIG. 17 depicts the plasma level profile of Risperidone in New Zealand rabbits provided by implants prepared according to Example 5. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIGS. 16 and 17. The results are expressed as the sum of the risperidone plus 9-OH-risperidone concentrations (ng/ml) as a function of time, since the therapeutic activity of 9-OH-risperidone is substantially equivalent to that of risperidone. As depicted in these figures, the injection of an amount of composition equivalent to 15 mg risperidone to New Zealand White rabbits resulted in poorly controlled plasma levels when a low inherent viscosity polymer, 0.20 and 0.22 dL/g was used (Formulations D and B, respectively). Composition D is incapable to satisfactorily control the initial drug release, eliciting high initial plasma levels and a subsequent fast decrease, whereas composition B cannot avoid an uncontrollable release, showing a profile with two plasma peaks. On the other hand, polymers with higher inherent viscosity (0.30-0.40 dL/g) induced moderate initial plasma levels during first 24 hours followed by sustained levels during at least 28 days.

Example 6: Different Inherent Viscosities of the Polymer for the Drug Letrozole In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|---|
| | | | | | Drug | Polymer | Solvent | |
| A | Letrozole | 50:50 | 0.43 | DMSO | 25 | 63.9 | 149.1 | 1.62 |
| B | Letrozole | 75:25 | 0.20 | DMSO | 25 | 85.2 | 127.8 | 0.43 |

-continued

| Formulation | Drug | Polymer lactic/glycolic ratio | Polymer Inherent Viscosity (dL/g) | Solvent | Component Amount (mg) Drug | Polymer | Solvent | Polymer Solution Viscosity (Pa·s) |
|---|---|---|---|---|---|---|---|---|
| C | Letrozole | 75:25 | 0.38 | DMSO | 25 | 63.9 | 149.1 | 0.66 |
| D | Letrozole | 100:0 | 0.30 | DMSO | 25 | 85.2 | 127.8 | 1.20 |

The implantable formulations were prepared by completely dissolving the polymer in the solvent and subsequently adding the drug in said polymeric solution.

Figure 18:
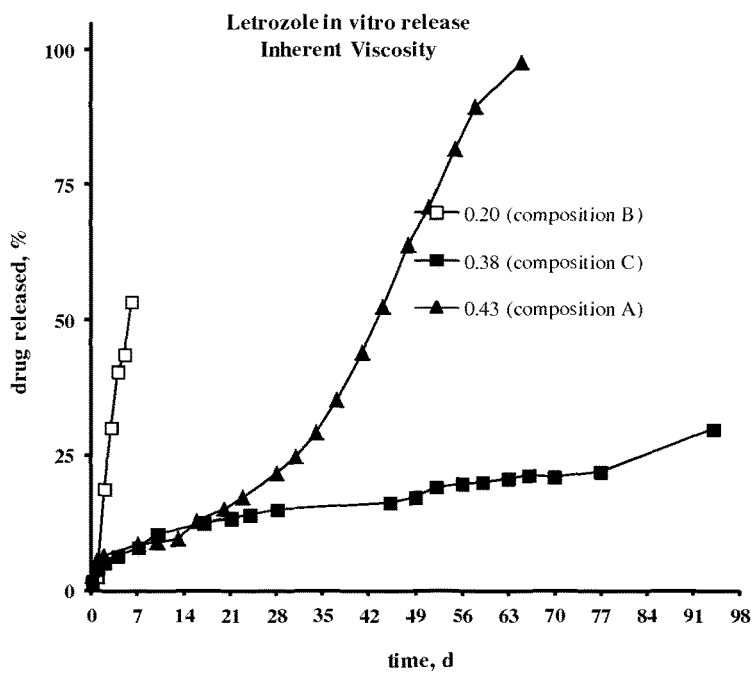
FIG. 18 depicts the release profile of Letrozole from implants prepared according to Example 6. Results are expressed as % Letrozole released from implants as a function of time.

In Vitro Release Profile:

The drug release from composition A, B and C of this example was evaluated according to the following procedure: The amount of formulation corresponding to 3 mg of letrozole was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 94 d depending on the profile), 5 ml of release medium was collected and replaced with fresh buffer and the amount of letrozole present in the sample was determined by HPLC-FLD. The profile of letrozole released from the implants of this example is shown in FIG. 18. The results are expressed as % drug released from implants as a function of time.

As depicted in FIG. 18, the release of the letrozole is not controlled when a 0.20 dL/g inherent viscosity polymer (Formulation B) was used instead of 0.38 or 0.43 dL/g (Formulations C and A, respectively), the former showing a faster drug release probably due to high drug diffusion processes. On the other hand, 0.38 and 0.43 dL/g inherent viscosity polymers showed controlled drug release for at least 63 days or more (Formulation C).

In Vivo Plasma Levels after Intramuscular Administration to New Zealand Rabbit:

The letrozole compositions A, C and D of this example were injected intramuscularly to New Zealand White rabbits weighing an average of 3 kg. The amount injected corresponded to a dose of letrozole of 5.4 mg (composition A and C) or 16.2 mg (composition D), and the composition was placed intramuscularly in the left hind leg using a syringe with a 20 G needle. The total number of rabbits per composition was 3. After injection, plasma levels were obtained at 0, 4 h, 1 d, 2 d, 4 d, 7 d, 10 d and periodically up to 56 days.

Figure 19:
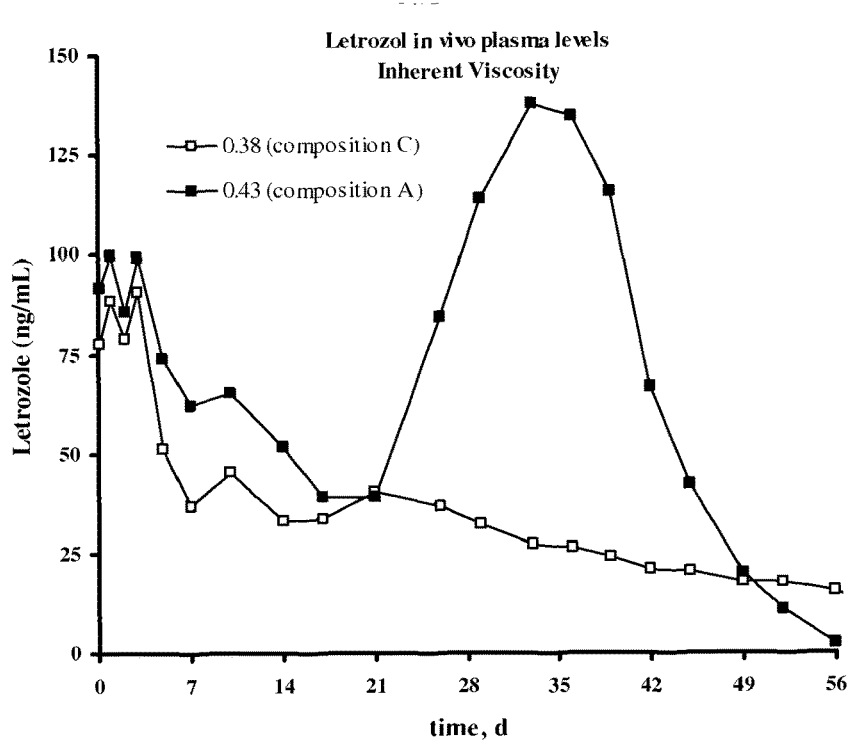
FIG. 19 depicts the plasma level profile of Letrozole in New Zealand rabbits provided by implants prepared according to Example 6. Results are expressed as the concentration of Letrozole as a function of time.
Figure 20:
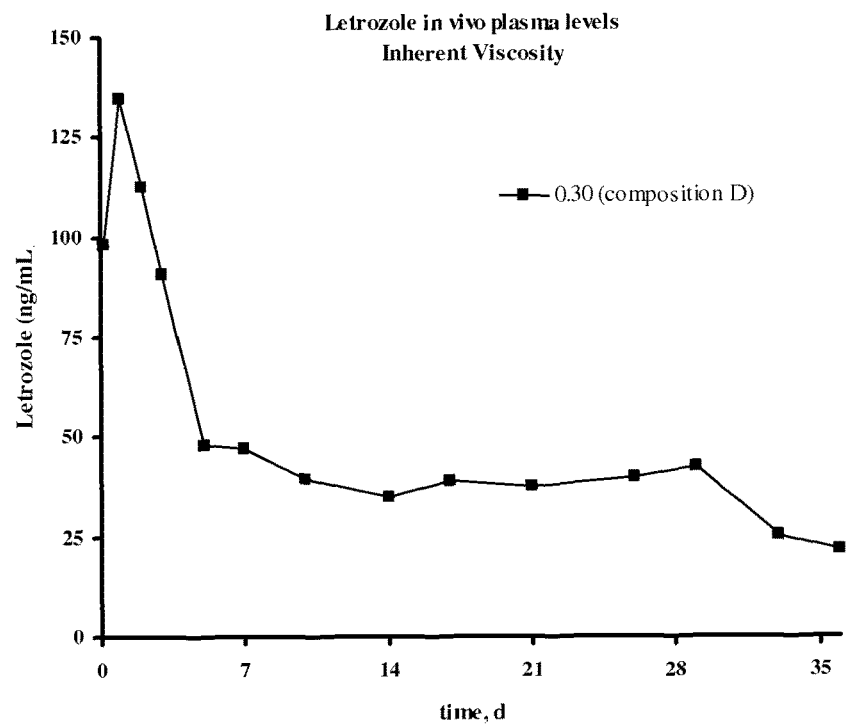
FIG. 20 depicts the plasma level profile of Letrozole in New Zealand rabbits provided by implants prepared according to Example 6. Results are expressed as the concentration of Letrozole as a function of time.

The kinetics of letrozole plasma levels corresponding to the each composition was evaluated. The profile of the plasma levels of letrozole is shown in FIG. 19 and FIG. 20. As depicted in FIG. 19, the injection of an amount of formulation equivalent to 5.4 mg letrozole to New Zealand White rabbits resulted in controlled initial plasma levels (first 3 days) with a duration period of at least 56 days when polymers having an inherent viscosity of 0.38-0.43 dL/g were used. Hence, an inherent viscosity of 0.30 dL/g (FIG. 20) resulted in an adequate control of the initial plasma levels followed by constant plasma levels for at least 35 days.

Example 7: Different Viscosities of the Polymeric Solution for the Drug Fentanyl In the present example, the composition of the implantable formulation was as follows:

| Formulation | Drug | Polymer lactic/glycolic ratio | Polymer Inherent Viscosity (dL/g) | Solvent | Component Amount (mg) Drug | Polymer | Solvent | Polymer Solution Viscosity (Pa·s) |
|---|---|---|---|---|---|---|---|---|
| A | Fentanyl | 50:50 | 0.40 | DMSO | 25 | 55 | 220 | 0.18 |
| B | Fentanyl | 50:50 | 0.40 | DMSO | 25 | 75 | 175 | 1.12 |
| C | Fentanyl | 50:50 | 0.40 | DMSO | 25 | 100 | 150 | 6.77 |

The implantable formulations were prepared by completely dissolving the polymer in the solvent and subsequently adding the drug in said polymeric solution.

Figure 21:
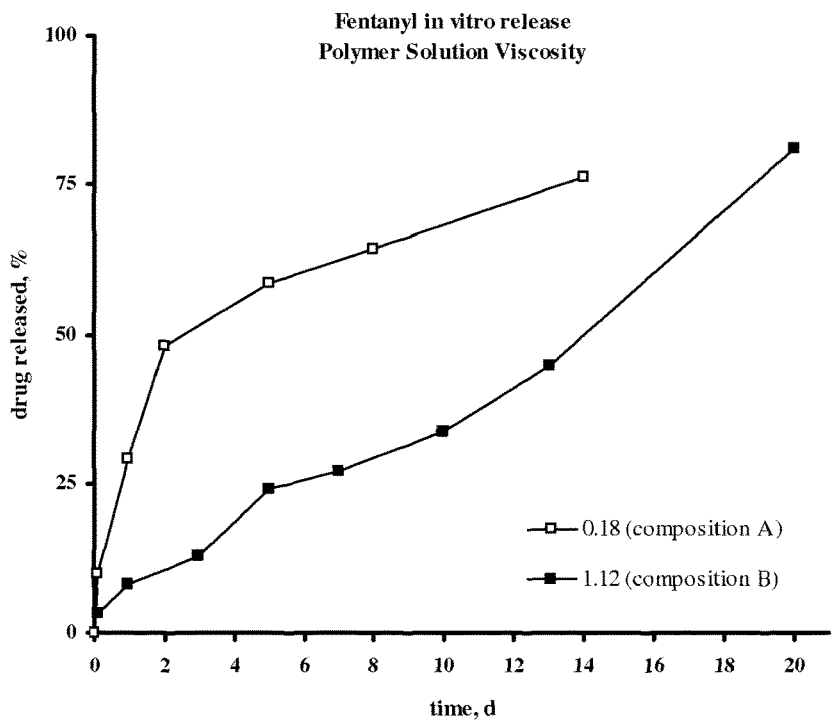
FIG. 21 depicts the release profile of Fentanyl from implants prepared according to Example 7. Results are expressed as % Fentanyl released from implants as a function of time.

In Vitro Release Profile:

The drug released from Formulations A and B of this example was evaluated according to the following procedure: The amount of formulation corresponding to 9 mg of fentanyl was injected from prefilled syringes into flasks having a pre-warmed release medium by using a 21 G needle. The release medium was 100 ml phosphate buffer pH=7.4. The flasks were then placed into an oven at 37° C. and kept under horizontal shaking at 50 rpm. At previously scheduled time points (2 h, 1 d, and periodically up to 20 d), 5 ml of release medium was collected and replaced with fresh buffer and the amount of fentanyl present in the sample was determined by UV spectrophotometry. The profile of fentanyl released from the implants of this example is shown in FIG. 21. The results are expressed as % drug released from implants as a function of time.

As depicted in FIG. 21, the release of the fentanyl it is better controlled when a polymer solution having a viscosity of 1.12 Pa·s is used instead of 0.18 Pa·s. The low viscosity polymer solution (Formulation A) fails to control the release of fentanyl, allowing a diffusion of 30% of the drug during the first 24 hours, whereas the higher viscosity polymer solution (composition B) allowed a controlled release for 21 days.

In Vivo Plasma Levels after Intramuscular Administration to New Zealand Rabbit:

The fentanyl Formulations B and C of this example were injected intramuscularly to New Zealand White rabbits weighing an average of 3 kg. The amount injected corresponded to a dose of 4.2 mg fentanyl, and the composition was placed intramuscularly in the left hind leg using a syringe with a 20 G needle. The total number of rabbits per composition was 3. After injection, plasma levels were obtained at 0, 4 h, 1 d, 2 d, 4 d, 7 d, 10 d and 14 d.

Figure 22:
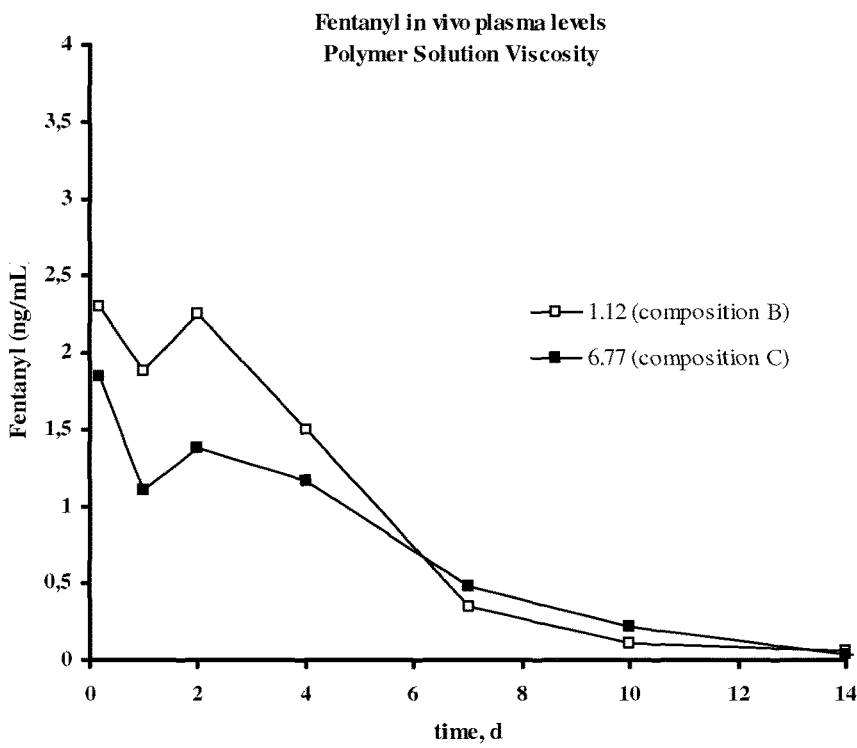
FIG. 22 depicts the plasma level profile of Fentanyl in New Zealand rabbits provided by implants prepared according to Example 7. Results are expressed as the concentration of Fentanyl as a function of time.

The kinetics of fentanyl plasma levels corresponding to the each composition was evaluated. The profile of the plasma levels of fentanyl is shown in FIG. 22. As it can be observed in this Figure, the injection of an amount of composition equivalent to 4.2 mg fentanyl to New Zealand White rabbits resulted in controlled initial plasma levels (first 3 days) when the viscosity of polymer solution of composition is in the range 1.12-6.77 Pa·s, and a duration of around 14 days.

Example 8: Different Viscosities of the Polymeric Solution for the Drug Olanzapine In the present example, the composition of the implantable formulation was as follows:

| Formulation | Drug | Polymer lactic/glycolic ratio | Polymer Inherent Viscosity (dL/g) | Solvent | Component Amount (mg) | | | Polymeric Solution Viscosity (Pa · s) |
|---|---|---|---|---|---|---|---|---|
| | | | | | Drug | Polymer | Solvent | |
| A | Olanzapine | 50:50 | 0.43 | DMSO | 25 | 33.3 | 66.7 | 3.16 |
| B | Olanzapine | 75:25 | 0.38 | DMSO | 25 | 50 | 116.6 | 0.66 |
| C | Olanzapine | 100:0 | 0.30 | DMSO | 25 | 25 | 50 | 0.46 |

The implantable formulations were prepared by completely dissolving the polymer in the solvent and subsequently adding the drug in said polymeric solution.

Figure 23:
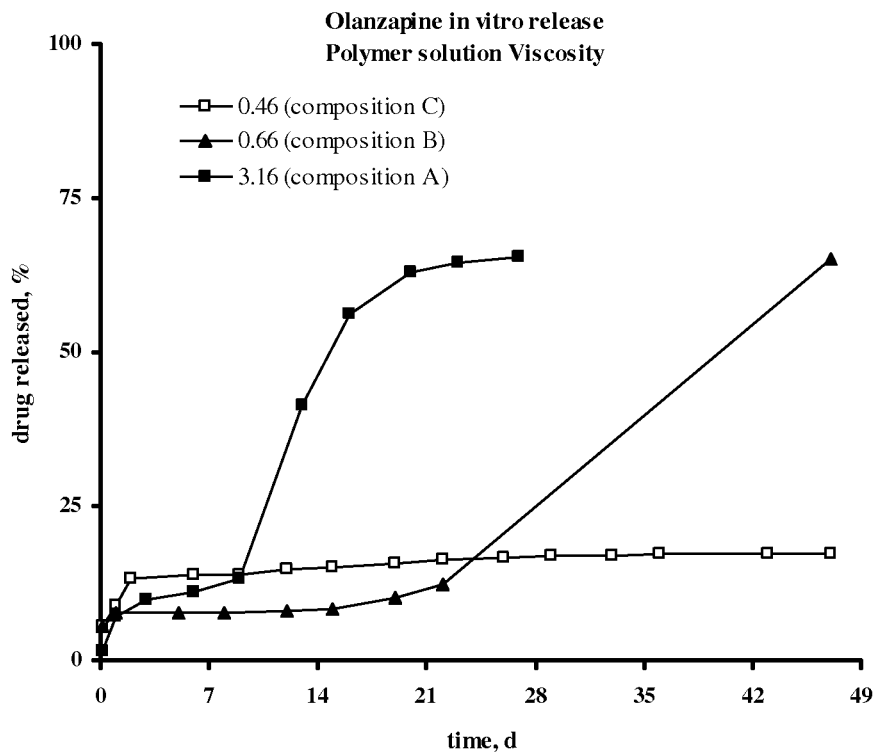
FIG. 23 depicts the release profile of Olanzapine from implants prepared according to Example 8. Results are expressed as % Olanzapine released from implants as a function of time.

In Vitro Release Profile:

The drug released from the formulations of this example was evaluated according to the following procedure: The amount of formulation corresponding to 10 mg of olanzapine was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 21 d or 49 d), 5 ml of release medium was collected and replaced with fresh buffer and the amount of olanzapine present in the sample was determined by UV spectrophotometry. The profile of olanzapine released from the implants of this example is shown in FIG. 23. The results are expressed as % drug released from implants as a function of time.

As depicted in FIG. 23, the release of the olanzapine is satisfactorily controlled at the initial moment and later on when polymers having different lactic/glycolic ratios (from 50:50 to 100:0) were used in formulations with a viscosity of the polymeric solution in the range of 0.46-3.16 Pa·s.

Example 9: Different Viscosities of the Polymeric Solution for the Drug Risperidone In the present example, the composition of the implantable formulation was as follows:

| Formulation | Drug | Polymer lactic/glycolic ratio | Polymer Inherent Viscosity (dL/g) | Solvent | Component Amount (mg) | | | Polymeric Solution Viscosity (Pa · s) |
|---|---|---|---|---|---|---|---|---|
| | | | | | Drug | Polymer | Solvent | |
| A | Risperidone | 50:50 | 0.40 | DMSO | 25 | 33.3 | 300 | 0.04 |
| B | Risperidone | 50:50 | 0.40 | DMSO | 25 | 66.7 | 266.6 | 0.18 |
| C | Risperidone | 50:50 | 0.40 | DMSO | 25 | 100 | 233.3 | 1.12 |
| D | Risperidone | 50:50 | 0.40 | DMSO | 25 | 133.3 | 200 | 6.77 |
| E | Risperidone | 75:25 | 0.38 | DMSO | 25 | 50 | 116.6 | 0.66 |
| F | Risperidone | 100:0 | 0.30 | DMSO | 25 | 50 | 116.6 | 0.26 |

The implantable formulations were prepared by completely dissolving the polymer in the solvent and subsequently adding the drug in said polymeric solution.

Figure 24:
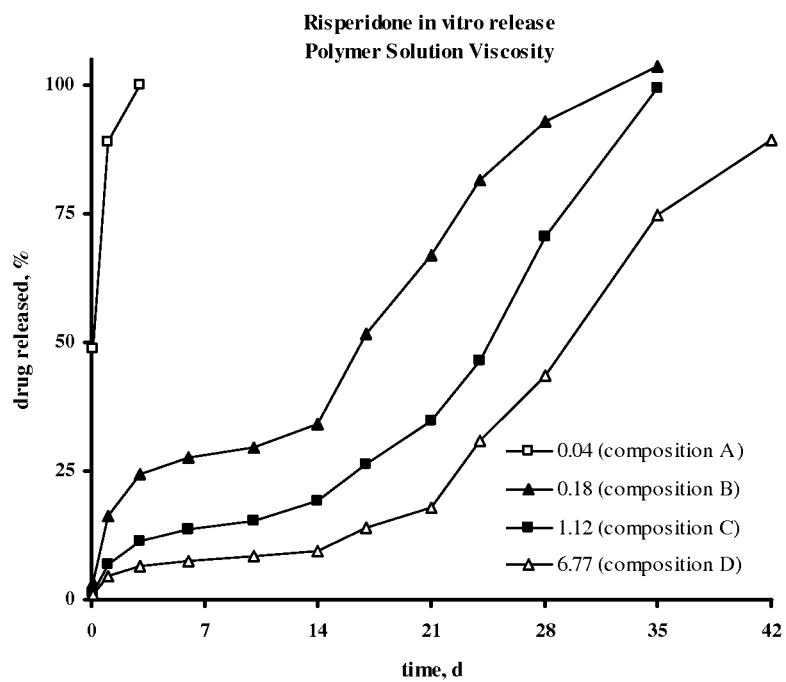
FIG. 24 depicts the release profile of Risperidone from implants prepared according to Example 9. Results are expressed as % Risperidone released from implants as a function of time.

In Vitro Release Profile:

The drug released from compositions A, B, C, and D of this example was evaluated according to the following procedure: The amount of formulation corresponding to 25 mg of risperidone was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 49 d), 5 ml of release medium was collected and replaced with fresh buffer and the amount of risperidone present in the sample was determined by UV spectrophotometry. The profile of risperidone released from the implants of this example is shown in FIG. 24. The results are expressed as % drug released from implants as a function of time.

As depicted in FIG. 24, the release of the risperidone it is absolutely not controlled when the viscosity of the polymer solution was 0.04 Pa·s, and not satisfactorily controlled in the case of 0.18 Pa·s, where an initial drug release higher than 15% during first 24 hours, and close to 25% during first 3 days, was observed. On the other hand, higher polymer solution viscosities, in this example 1.12 and 6.77 Pa·s, resulted in a suitable control of the drug release, allowing prolonged release times for at least 35 days.

In Vivo Plasma Levels after Intramuscular Administration to New Zealand Rabbit:

The risperidone Formulations C, D, E and F of this example were intramuscularly injected to New Zealand White rabbits weighing an average of 3 kg. The amount injected corresponded to a dose of 15 mg risperidone, and the composition was intramuscularly placed in the left hind leg using a syringe with a 20 G needle. The total number of rabbits per composition was 3. After injection, plasma levels were obtained at 0, 4 h, 1 d, 2 d, 5 d, 7 d, 10 d and periodically up to 35 days.

Figure 25:
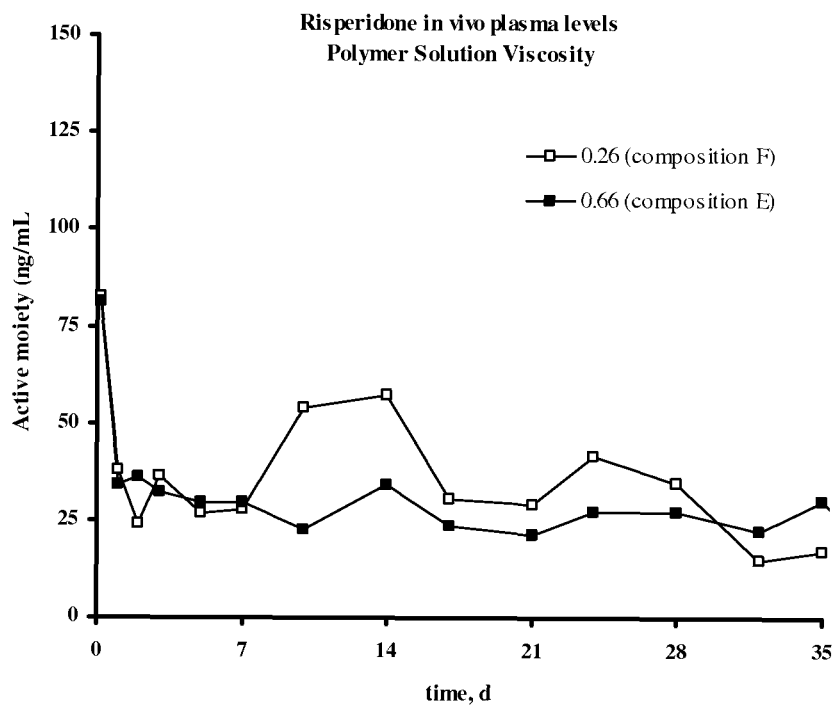
FIG. 25 depicts the plasma level profile of Risperidone in New Zealand rabbits provided by implants prepared according to Example 9. Results are expressed as the sum of the concentrations of Risperidone and its active metabolite 9-hydroxide-risperidone as a function of time.
Figure 26:
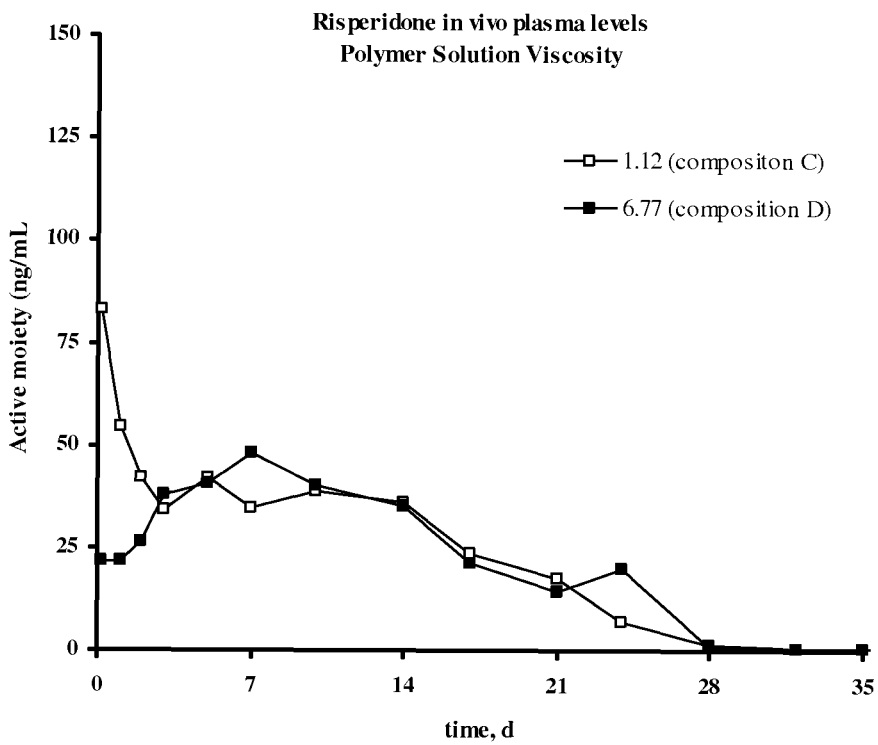
FIG. 26 depicts the plasma level profile of Risperidone in New Zealand rabbits provided by implants prepared according to Example 9. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIGS. 25 and 26. The results are expressed as the sum of the risperidone plus 9-OH-risperidone concentrations (ng/ml) as a function of time, since the therapeutic activity of 9-OH-risperidone is substantially equivalent to that of risperidone. As it can be observed in these Figures, the injection of an amount of composition equivalent to 15 mg risperidone to New Zealand White rabbits resulted in satisfactorily controlled plasma levels in all cases when polymer solution viscosities in the range 0.26-6.77 Pa·s where used, thereby providing therapeutic plasma levels after 4 hours, and sustained plasma levels from the 3rd day until at least 21 days.

Figure 27:
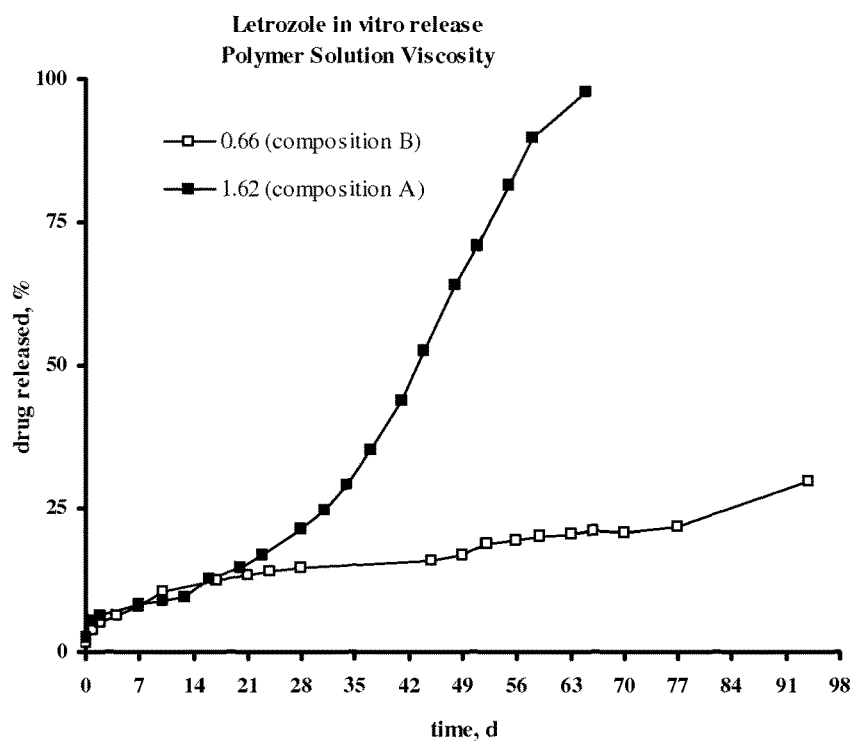
FIG. 27 depicts the release profile of Letrozole from implants prepared according to Example 10. Results are expressed as % Letrozole released from implants as a function of time.
Figure 28:
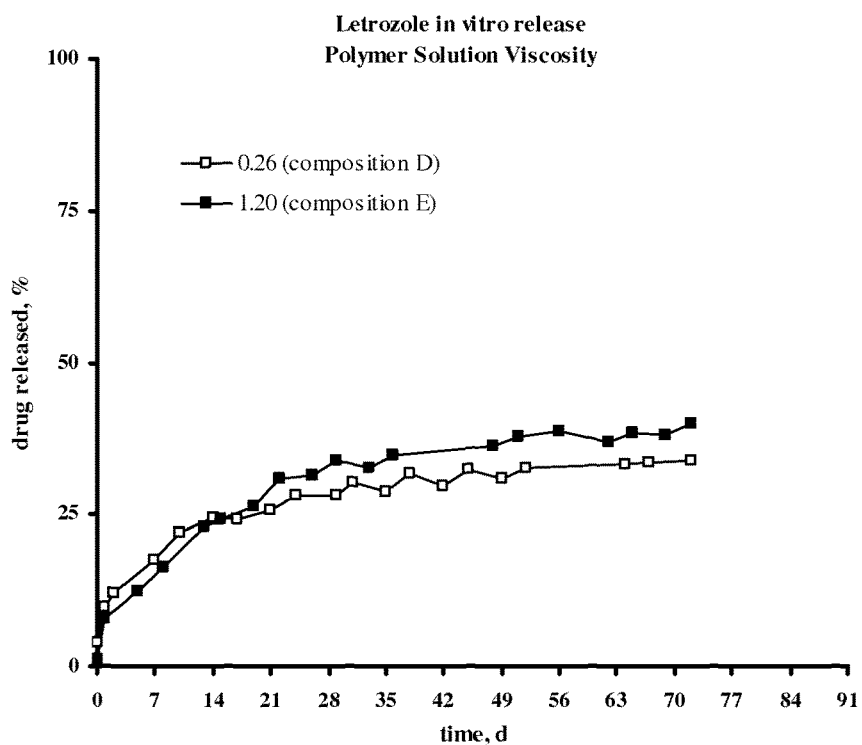
FIG. 28 depicts the release profile of Letrozole from implants prepared according to Example 10. Results are expressed as % Letrozole released from implants as a function of time.

Example 10: Different Viscosities of the Polymeric Solution for the Drug Letrozole In the present example, the composition of the implantable formulation was as follows:

needle. The release medium was 250 ml phosphate buffer pH=7.4. The flasks were then placed into an oven at 37° C. and kept under horizontal shaking at 50 rpm. At previously scheduled time points (2 h, 1 d, and periodically depending on the obtained profile), 5 ml of release medium was collected and replaced with fresh buffer and the amount of letrozole present in the sample was determined by HPLC-FLD. The profile of letrozole released from the implants of this example is shown in FIG. 27 and FIG. 28. The results are expressed as % drug released from implants as a function of time.

As depicted in these figures, the release of the letrozole is satisfactorily controlled in all cases where polymeric solutions having a viscosity in the range 0.26-1.62 Pa·s were used. All the formulations showed an initial release below 10% during first day. As FIG. 27 shows, both 50:50 (Composition A) and 75:25 (Composition B) lactic/glycolic polymer satisfactorily control the release of letrozole, although the release rate was logically slower (with a consequent longer duration period) for the 75:25 polymer. A polymer with a 100:0 lactic/glycolic ratio (FIG. 28, Compositions D and E) also resulted in a satisfactory initial and sustained control.

In Vivo Plasma Levels after Intramuscular Administration to New Zealand Rabbit:

The letrozole compositions A, C and E of this example were injected intramuscularly to New Zealand White rabbits weighing an average of 3 kg. The amount injected corresponded to a dose of letrozole of 5.4 mg (Formulation A) or 16.2 mg (Formulations C and E), and the composition was placed intramuscularly in the left hind leg using a syringe with a 20 G needle. The total number of rabbits per composition was 3. After injection, plasma levels were obtained at 0, 4 h, 1 d, 2 d, 3 d, 5 d, 7 d, 10 d and periodically up to 56 days.

Figure 29:
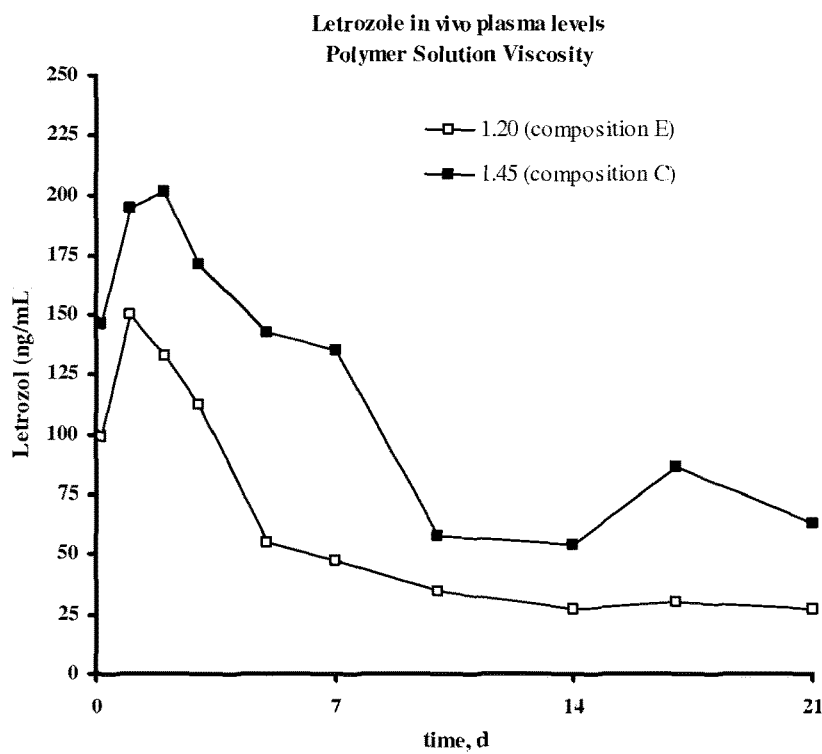
FIG. 29 depicts the plasma level profile of Letrozole in New Zealand rabbits provided by implants prepared according to Example 10. Results are expressed as the concentration of Letrozole as a function of time.
Figure 30:
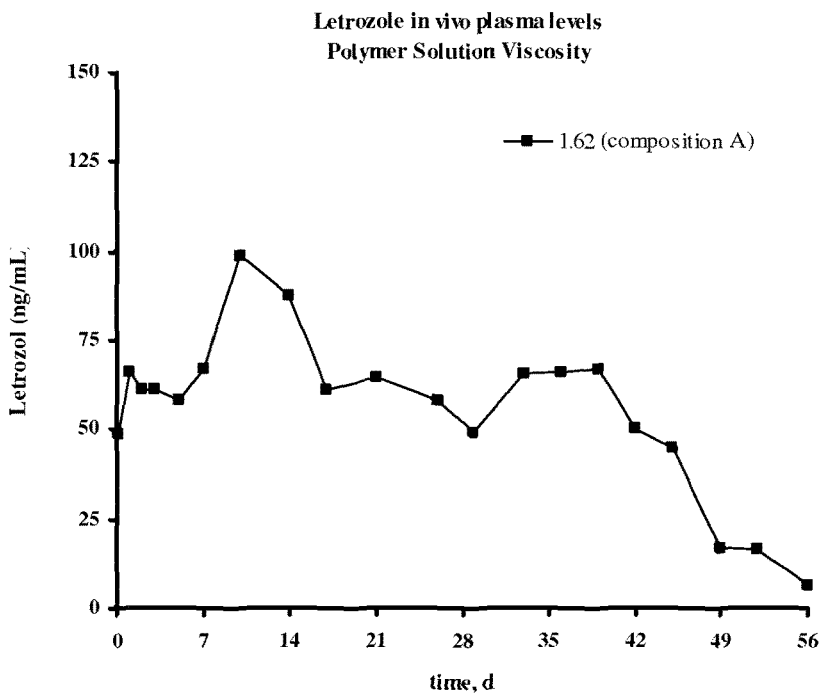
FIG. 30 depicts the plasma level profile of Letrozole in New Zealand rabbits provided by implants prepared according to Example 10. Results are expressed as the concentration of Letrozole as a function of time.

The kinetics of letrozole plasma levels corresponding to the each composition was evaluated. The profile of the plasma levels of letrozole is shown in FIG. 29 and FIG. 30. As depicted in FIG. 29, the injection of an amount of composition equivalent to 16.2 mg letrozole to New Zealand White rabbits resulted in controlled initial plasma levels

| Formulation | Drug | Polymer lactic/glycolic ratio | Polymer Inherent Viscosity (dL/g) | Solvent | Component Amount (mg) | | | Polymeric Solution Viscosity (Pa · s) |
|---|---|---|---|---|---|---|---|---|
| | | | | | Drug | Polymer | Solvent | |
| A | Letrozole | 50:50 | 0.43 | DMSO | 25 | 63.9 | 149.1 | 1.62 |
| B | Letrozole | 75:25 | 0.38 | DMSO | 25 | 63.9 | 149.1 | 0.66 |
| C | Letrozole | 75:25 | 0.38 | DMSO | 25 | 74.6 | 138.4 | 1.45 |
| D | Letrozole | 100:0 | 0.30 | DMSO | 25 | 63.9 | 149.1 | 0.26 |
| E | Letrozole | 100:0 | 0.30 | DMSO | 25 | 85.2 | 127.8 | 1.20 |

The implantable formulations were prepared by completely dissolving the polymer in the solvent and subsequently adding the drug in said polymeric solution.

In Vitro Release Profile:

The drug released from Formulations A, B, D and E of this example was evaluated according to the following procedure: The amount of formulation corresponding to 3 mg of letrozole was injected from prefilled syringes into flasks having a pre-warmed release medium by using a 21 G (first 3 days) with a duration period of at least 21 days when the viscosity of the polymer solution was 1.20-1.45 Pa·s, and using 75:25 or 100:0 lactic/glycolic polymers. Also, the injection of an amount of composition equivalent to 5.4 mg letrozole with a composition involving a polymer solution viscosity of 1.62 Pa·s (FIG. 30) resulted in satisfactorily controlled initial plasma levels followed by constant plasma levels for at least 42 days using a 50:50 lactic/glycolic polymer.

Comparative Examples 2-3: Implantable Formulations Including a Low Water Miscible Solvent (Example not According to the Invention)

In the present example, the composition of the implantable formulation was as follows:

| Formulation | Drug | Polymer lactic/glycolic ratio | Polymer Inherent Viscosity (dL/g) | Solvent | Component Amount (mg) | | | Polymeric Solution Viscosity (Pa · s) |
|---|---|---|---|---|---|---|---|---|
| | | | | | Drug | Polymer | Solvent | |
| A | Fentanyl | 75:25 | 0.20 | BB | 25 | 150 | 350 | 1.25 |
| B | Fentanyl | 75:25 | 0.20 | BA | 25 | 200 | 300 | 1.05 |
| C | Fentanyl | 75:25 | 0.20 | AA | 25 | 250 | 250 | 1.58 |
| D | Olanzapine | 75:25 | 0.38 | BB | 25 | 50 | 116.6 | 6.45 |
| E | Risperidone | 75:25 | 0.20 | BB | 25 | 100 | 233.3 | 1.25 |
| F | Risperidone | 75:25 | 0.20 | BA | 25 | 133.3 | 200 | 1.05 |
| G | Letrozole | 75:25 | 0.38 | BB | 25 | 50 | 116.6 | 6.45 |

BB: benzyl benzoate
BA: benzyl alcohol
AA: acetic acid

Figure 31:
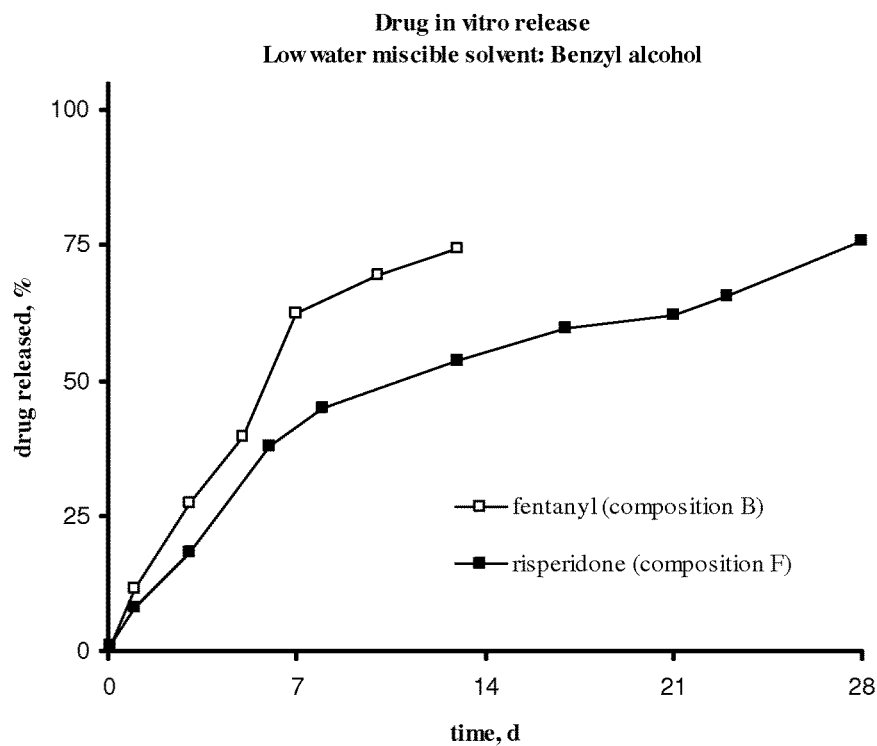
FIG. 31 depicts the release profile of Fentanyl and Risperidone from implants prepared according to Comparative Examples 2-3. Results are expressed as % drug released from implants as a function of time.
Figure 32:
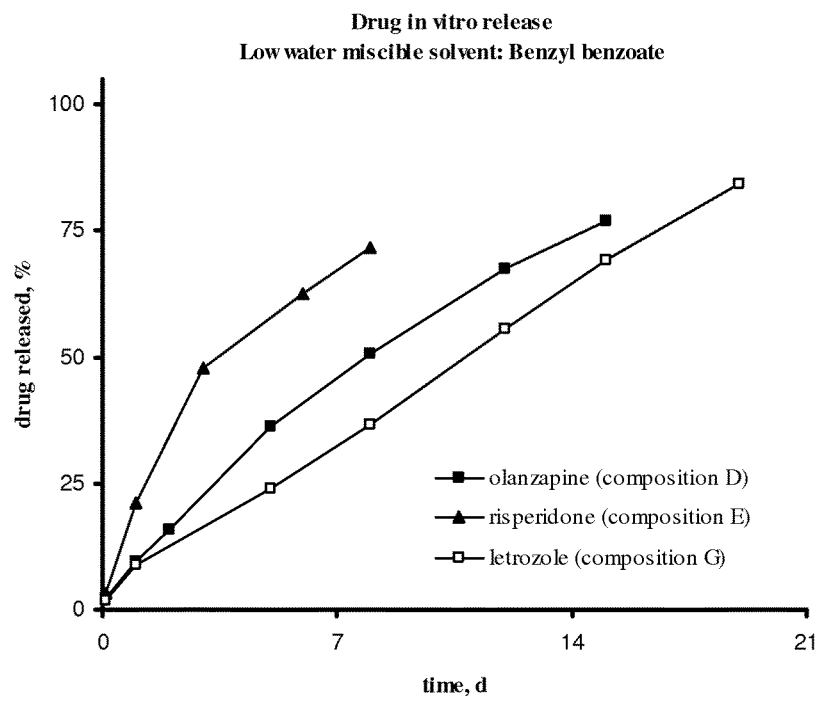
FIG. 32 depicts the release profile of Olanzapine, Risperidone and Letrozole from implants prepared according to Comparative Examples 2-3. Results are expressed as % drug released from implants as a function of time.

In Vitro Release Profile:

The drug release from compositions B, D, E, F, and G of this example was evaluated according to the following procedure, variable depending on the formulated drug: The amount of formulation corresponding to 9, 10, 25 or 3 mg of fentanyl, olanzapine, risperidone or letrozole was injected from prefilled syringes into flasks having a pre-warmed release medium by using a 21 G needle. The release medium was phosphate buffer pH=7.4 (100 ml for fentanyl and 250 ml for the remaining drugs). The flasks were then placed into an oven at 37° C. and kept under horizontal shaking at 50 rpm. At previously scheduled time points (2 h, 1 d, and periodically up to 28 days, depending of each compostions), 5 ml of release medium was collected and replaced with fresh buffer and the amount of drug present in the sample was determined by UV spectrophotometry (fentanyl, olanzapine, risperidone) or HPLC-FLD (letrozole). The profile of drug released from the implants of this example is shown in FIG. 31 and FIG. 32. The results are expressed as % drug released from implants as a function of time.

As depicted in these figures, low water miscible solvents such as benzyl benzoate and benzyl alcohol resulted unsuitable for their use in injectable long lasting implantable systems according to the invention, since their drug release profile is too fast for the desired targets, and resulted uncontrollable, as it can be observed based on the high initial drug release during first days.

In Vivo Plasma Levels after Intramuscular Administration to New Zealand Rabbit:

The fentanyl and risperidone formulations of this example were injected intramuscularly to New Zealand White rabbits weighing an average of 3 kg. The amount injected corresponded to a dose of 4.2 mg fentanyl or 15 mg risperidone, and the composition was placed intramuscularly in the left hind leg using a syringe with a 20 G needle. The total number of rabbits per composition was 3. After injection, plasma levels were obtained at 0, 4 h, 1 d, 2 d, and periodically up to 14 d and 28 d, respectively.

Figure 33:
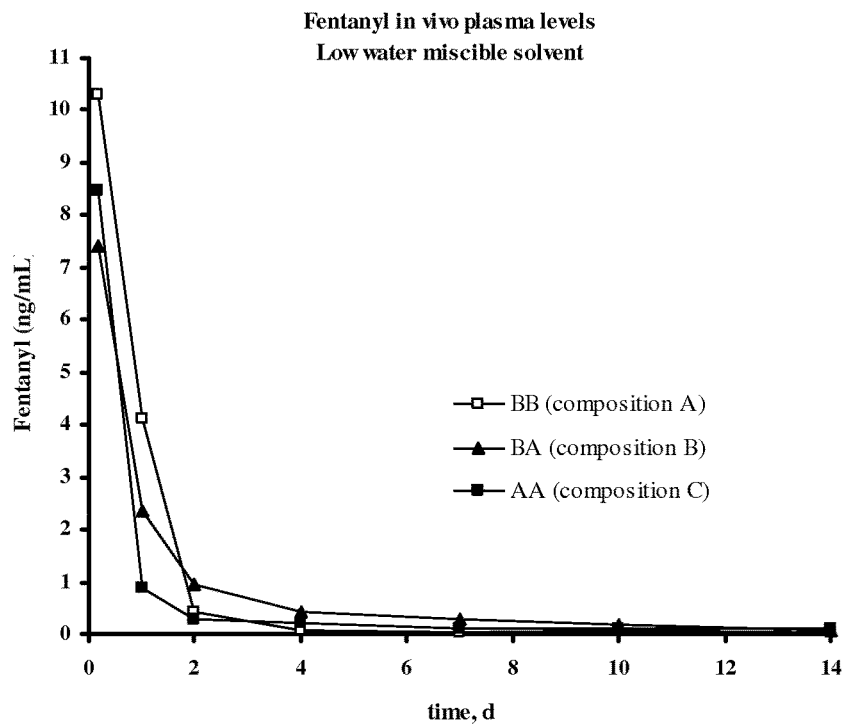
FIG. 33 depicts the plasma level profile of Fentanyl in New Zealand rabbits provided by implants prepared according to Comparative Examples 2-3. Results are expressed as the concentration of Fentanyl as a function of time.
Figure 34:
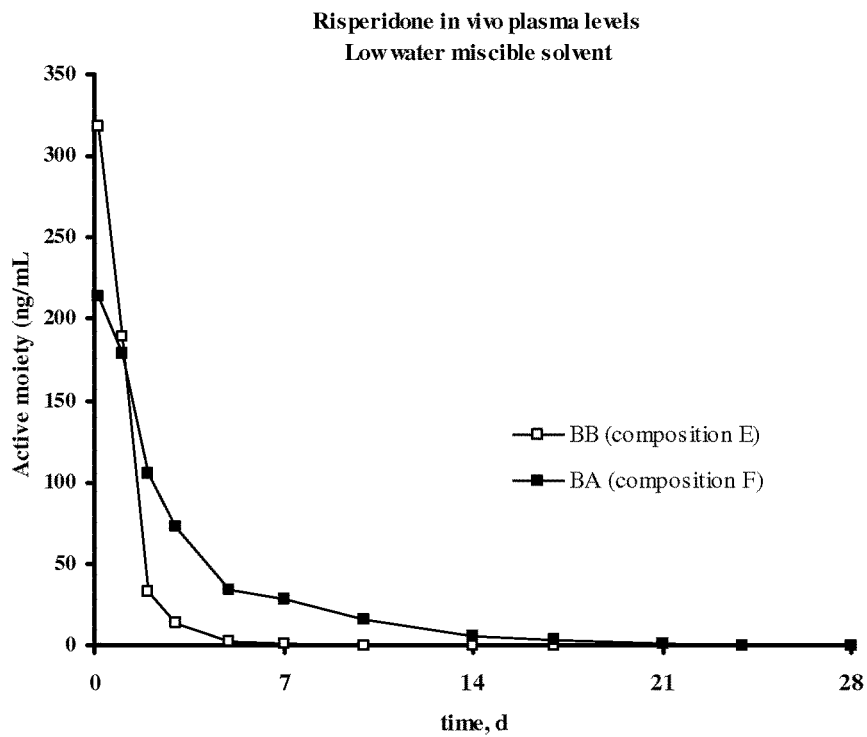
FIG. 34 depicts the plasma level profile of Risperidone in New Zealand rabbits provided by implants prepared according to Comparative Examples 2-3. Results are expressed as the sum of the concentrations of Risperidone and its active metabolite 9-hydroxide-risperidone as a function of time.

The kinetics of the drug plasma levels corresponding to the each composition was evaluated. The profile of the plasma levels of the fentanyl and risperidone (active moiety, corresponding to risperidone plus its pharmacologically equivalent metabolite 9-OH-risperidone) is shown in FIG. 33 and FIG. 34, respectively. As depicted in FIG. 33, fentanyl implantable compositions based in low water miscible solvents as benzyl benzoate, benzyl alcohol and acetic acid evoke huge initial plasma levels during first day, followed by a fast release with almost no levels from the 2$^{nd}$ day. In the case of risperidone (FIG. 34), the use of same low water miscible solvents result in very high initial plasma levels (first 4 hours) and, as for fentanyl, followed by a very fast decrease to low plasma levels, therefore failing to achieve the objective of sustained plasma levels during at least 14 days.

Example 11: Use of Different Water-Soluble Solvents Having Different Polarities for Drug Fentanyl In the present example, the composition of the implantable formulation was as follows:

| Formulation | Drug | Polymer lactic/glycolic ratio | Polymer Inherent Viscosity (dL/g) | Solvent | Component Amount (mg) | | | Polymeric Solution Viscosity (Pa · s) |
|---|---|---|---|---|---|---|---|---|
| | | | | | Drug | Polymer | Solvent | |
| A | Fentanyl | 50:50 | 0.40 | NMP | 25 | 150 | 350 | 1.08 |
| B | Fentanyl | 50:50 | 0.40 | DMSO | 25 | 150 | 350 | 1.12 |

The implantable formulations were prepared by completely dissolving the polymer in the solvent and subsequently adding the drug in said polymeric solution.

Figure 35:
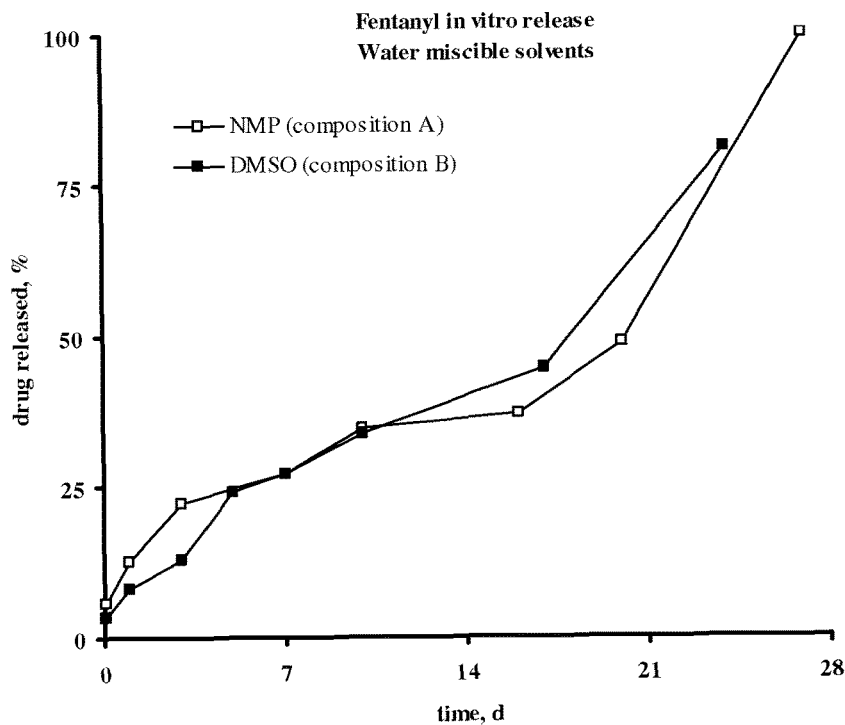
FIG. 35 depicts the release profile of Fentanyl from implants prepared according to Example 11. Results are expressed as % Fentanyl released from implants as a function of time.

In Vitro Release Profile:

The drug released from the formulations of this example was evaluated according to the following procedure: The amount of formulation corresponding to 9 mg of fentanyl was injected from prefilled syringes into flasks having a pre-warmed release medium by using a 21 G needle. The release medium was 100 ml phosphate buffer pH=7.4. The flasks were then placed into an oven at 37° C. and kept under horizontal shaking at 50 rpm. At previously scheduled time points (2 h, 1 d, and periodically up to 20 d), 5 ml of release medium was collected and replaced with fresh buffer and the amount of fentanyl present in the sample was determined by UV spectrophotometry. The profile of fentanyl released from the implants of this example is shown in FIG. 35. The results are expressed as % drug released from the implants as a function of time.

As depicted in FIG. 35, the release of the fentanyl is well controlled and sustained for at least 21 days when the solvent used, probably due to its high water miscibility, shows certain polarity characteristics such as large dipole moment (3.7-4.5 D) and high dielectric constant (30-50) as those used in this example.

Example 12: Use of Different Water-Soluble Solvents Having Different Polarities for the Drug Risperidone In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|---|
| | | | | | Drug | Polymer | Solvent | |
| A | Risperidone | 50:50 | 0.40 | Dioxane | 25 | 100 | 233.3 | 2.50 |
| B | Risperidone | 50:50 | 0.40 | NMP | 25 | 100 | 233.3 | 1.08 |
| C | Risperidone | 50:50 | 0.40 | DMSO | 25 | 100 | 233.3 | 1.12 |

The implantable formulations were prepared by completely dissolving the polymer in the solvent and subsequently adding the drug in said polymeric solution.

Figure 36:
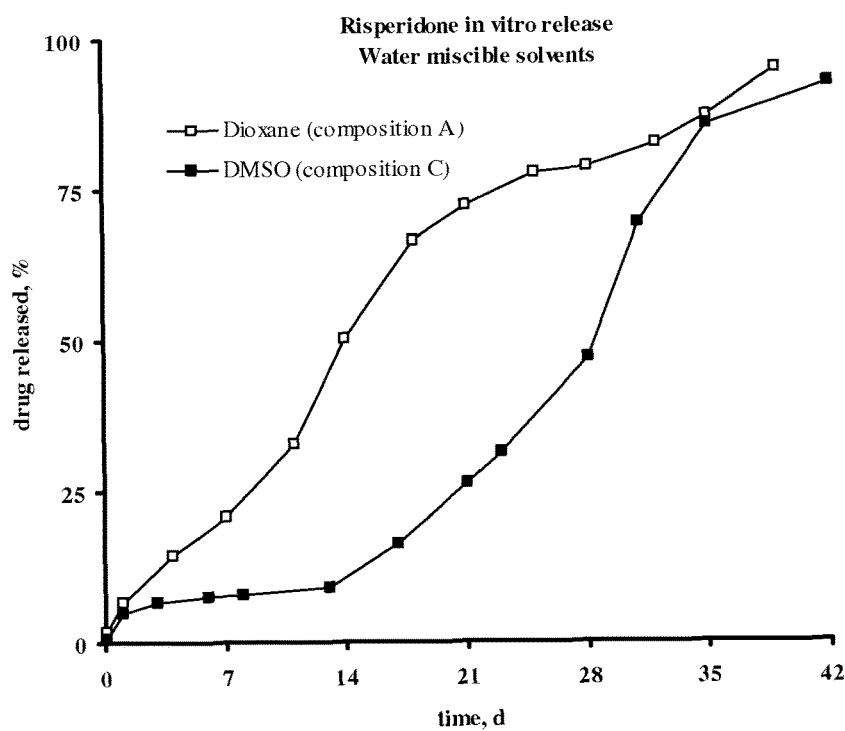
FIG. 36 depicts the release profile of Risperidone from implants prepared according to Example 12. Results are expressed as % Risperidone released from implants as a function of time.

In Vitro Release Profile:

The drug released from the formulations of this example was evaluated according to the following procedure: The amount of formulation corresponding to 25 mg of risperidone was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 42 d), 5 ml of release medium was collected and replaced with fresh buffer and the amount of risperidone present in the sample was determined by UV spectrophotometry. The profile of risperidone released from the implants of this example is shown in FIG. 36. The results are expressed as % drug released from implants as a function of time.

As depicted in FIG. 36, the release of the risperidone is better controlled when DMSO was used as solvent rather than dioxane: The initial release is lower in the case of DMSO, and very significant differences among the solvents tested were observed during first 7 days. When DMSO is used, the formulation is capable of retaining a sustainable drug diffusion during at least 14 days. On the other hand, a continuous drug diffusion was observed when dioxane was used, thus resulting in faster releases and lower duration time periods for the possible therapeutic effect. This fact reveals that the water miscibility is not the only characteristic of the solvent to take into account in order to design and develop injectable in situ implantable formulations. The use of high polar solvents (DMSO) instead of lower ones (Dioxane) induces a faster implant hardening and thus originating a lower drug diffusion during implant formation.

In Vivo Plasma Levels after Intramuscular Administration to New Zealand Rabbit:

The risperidone compositions B and C of this example were injected intramuscularly to New Zealand White rabbits weighing an average of 3 kg. The amount injected corresponded to a dose of 15 mg risperidone, and the composition was placed intramuscularly in the left hind leg using a syringe with a 20 G needle. The total number of rabbits per composition was 3. After injection, plasma levels were obtained at 0, 4 h, 1 d, 2 d, 5 d, 7 d, 10 d and periodically up to 35 days.

Figure 37:
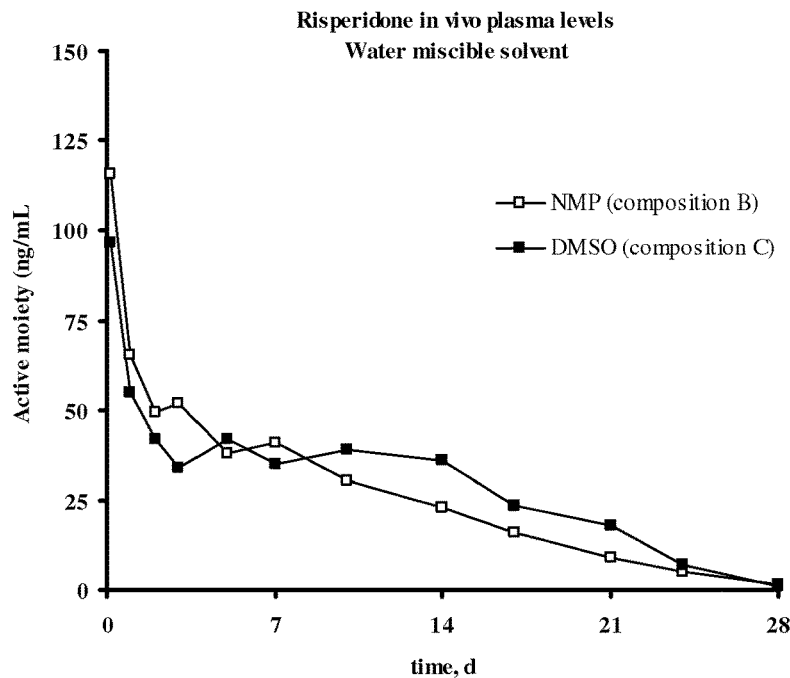
FIG. 37 depicts the plasma level profile of Risperidone in New Zealand rabbits provided by implants prepared according to Example 12. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 37. The results are expressed as the sum of the risperidone plus 9-OH-risperidone concentrations (ng/ml) as a function of time, since the therapeutic activity of 9-OH-risperidone is substantially equivalent to that of risperidone. As it can be observed in this Figure, the injection of an amount of composition equivalent to 15 mg risperidone to New Zealand White rabbits resulted in well controlled initial plasma levels (first 3 days) when high polar aprotic water miscible solvents having a dipole moment 3.7-4.5 D and dielectric constant 30-50 is used. This is in accordance with previously presented results regarding in vitro release of both fentanyl and risperidone, where as expected, solvents which show a controlled and sustained in vitro release have the capacity to reproduce the same behaviour following in vivo administration, and eliciting initial controlled and sustained plasma levels for at least 21 days, thus minimizing the difference between Cmax and Cmin plasma levels.

Example 13: Use of Different Water-Soluble Solvents Having Different Polarities for the Drug Letrozole In the present example, the composition of the implantable formulation was as follows:

| Formulation | Drug | Polymer lactic/glycolic ratio | Polymer Inherent Viscosity (dL/g) | Solvent | Component Amount (mg) | | | Polymer Solution Viscosity (Pa · s) |
|---|---|---|---|---|---|---|---|---|
| | | | | | Drug | Polymer | Solvent | |
| A | Letrozole | 50:50 | 0.40 | NMP | 25 | 50 | 116.6 | 1.08 |
| B | Letrozole | 50:50 | 0.40 | DMSO | 25 | 50 | 116.6 | 1.12 |

The implantable formulations were prepared by completely dissolving the polymer in the solvent and subsequently adding the drug in said polymeric solution.

Figure 38:
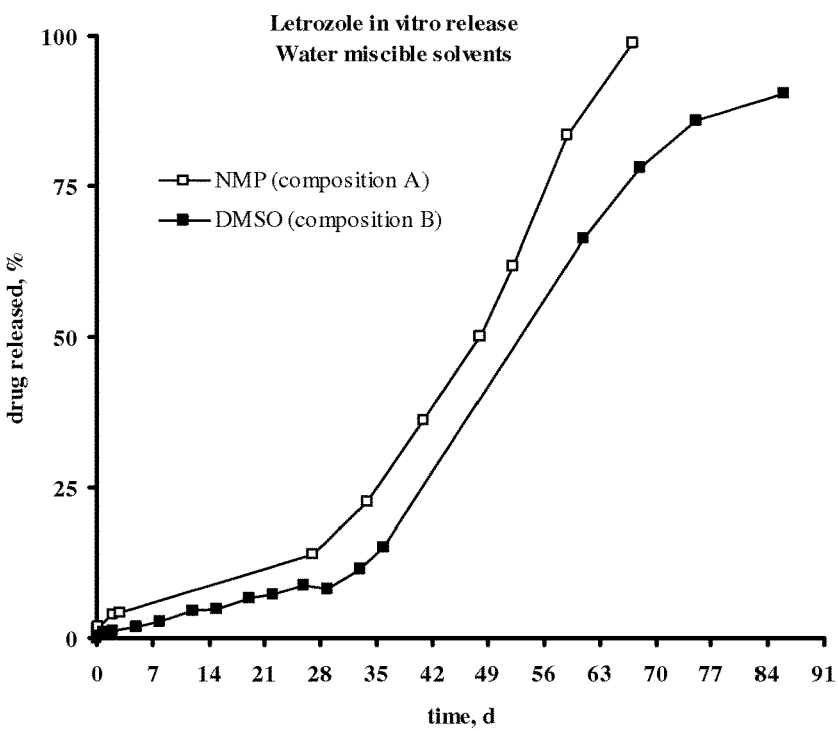
FIG. 38 depicts the release profile of Letrozole from implants prepared according to Example 13. Results are expressed as % Letrozole released from implants as a function of time.

In Vitro Release Profile:

The drug released from the formulations of this example was evaluated according to the following procedure: The amount of formulation corresponding to 3 mg of letrozole was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 31 d), 5 ml of release medium was collected and replaced with fresh buffer and the amount of letrozole present in the sample was determined by HPLC-FLD. The profile of letrozole released from the implants of this example is shown in FIG. 38. The results are expressed as % drug released from implants as a function of time.

As it can be observed in the FIG. 38, and in accordance with Examples 14 and 15, the release of the letrozole is well controlled when water miscible solvents having a large dipole moment (3.7-4.5 D) and dielectric constant (30-50) such as NMP and DMSO are used instead of lower polar solvents (Dioxane), the latter showing a faster diffusion to body liquids and thus a faster hardening of the implant, especially during the initial release, therefore reducing the drug diffusion phenomenon.

Example 14: Study of the Addition of a pH Modifier

The same risperidone implantable formulations were prepared by completely dissolving the polymer in the solvent (DMSO) and subsequently dispersing the drug in the mentioned polymeric solution with the optional addition of an alkaline agent such magnesium hydroxide.

| Ingredient | Amount (mg) | |
|---|---|---|
| | No Alkaline agent | Alkaline agent |
| PLGA polymer | 100 | 100 |
| Risperidone | 25 | 25 |
| Dimethyl sulfoxide (solvent) | 233.3 | 233.3 |
| Magnesium Hydroxide | — | 8.3 |

Polymer corresponds to a 50:50 lactic/glycolic, inherent viscosity 0.40 dL/g polymer.

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. The total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 39:
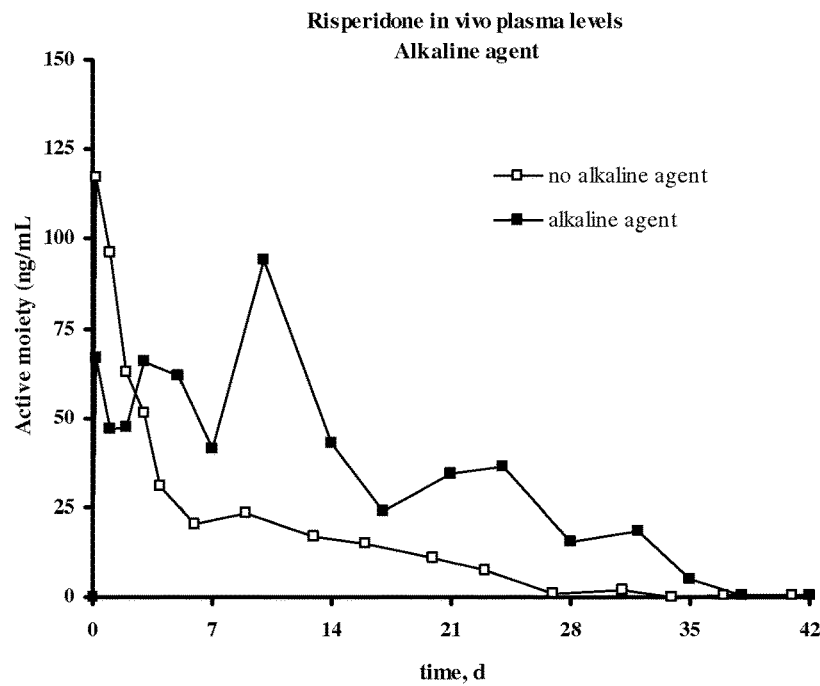
FIG. 39 depicts the plasma level profile of Risperidone in New Zealand rabbits provided by implants prepared according to Example 14. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 39. The results are expressed as the sum of the risperidone plus 9-OH-risperidone concentrations (ng/ml) as a function of time, since the therapeutic activity of 9-OH-risperidone is substantially equivalent to that of risperidone. As shown in the cited figure, the injection of an amount of formulation corresponding to 15 mg risperidone to New Zealand White rabbits resulted in initial plasma levels starting from 4 h post-administration up to at least 23 days. However, by the use of an alkaline agent within the polymer matrix, a more sustained plasma levels starting from 4 h post-administration, and an enlargement of the time where therapeutic risperidone plasma levels is achieved, up to at least 32 days.

Example 15: Study of the Effect of Sterilization by Irradiation

In the present example, the composition of the risperidone implantable formulations was as follows, always maintaining the same amounts of drug, polymer and solvent:

| Formulation | Irradiation (KGy) | Polymer lactic/glycolic ratio | Polymer Mean Mw (g/mol) | Polymer Inherent Viscosity (dL/g) | Solvent | Component Amount (mg) | | | Polymer Solution Viscosity (Pa · s) |
|---|---|---|---|---|---|---|---|---|---|
| | | | | | | Drug | Polymer | Solvent | |
| A | 0 | 50:50 | 27,020 | 0.20-0.43 | DMSO | 25 | 50 | 116.6 | 1.62 |
| B | 10 | 50:50 | 23,839 | 0.20-0.43 | DMSO | 25 | 50 | 116.6 | 1.30 |
| C | 15 | 50:50 | 22,182 | 0.20-0.43 | DMSO | 25 | 50 | 116.6 | 1.00 |
| D | 25 | 50:50 | 20,991 | 0.20-0.43 | DMSO | 25 | 50 | 116.6 | 0.81 |
| E | 0 | 50:50 | 39,708 | 0.20-0.58 | DMSO | 25 | 50 | 116.6 | 6.16 |
| F | 15 | 50:50 | 30,985 | 0.20-0.50 | DMSO | 25 | 50 | 116.6 | 2.66 |
| G | 25 | 50:50 | 27,891 | 0.20-0.50 | DMSO | 25 | 50 | 116.6 | 1.78 |

The implantable formulations were prepared by direct reconstitution of the contents of 2 prefilled syringes, a first one with a mixture of polymer and risperidone, and a second one with the solvent. The syringes were connected.

The syringe containing polymer plus risperidone mixtures was sterilized by β-irradiation in the range 5-25 KGy. As shown in the table, two different polymers were tested, one being a 50:50 polymer with mean Mw 27,020 g/mol, either non-irradiated or irradiated at 10, 15 or 25 Kgy (Formulations A-D), and the other one being a polymer with mean Mw 39,708 g/mol, either non-irradiated or irradiated at 15 or 25 Kgy (Formulations E-G).

Formulations A and E received sterilization irradiations evoking different compositions due to the losses in polymer molecular weight during the process. However, the resulting inherent viscosity was never below 0.20 dL/g in any case, and the polymer solution viscosity was maintained between the range 0.26-6.77 Pa·s, which range was previously studied and found adequate for this kind of long lasting implantable formulations (Example 9).

Figure 40:
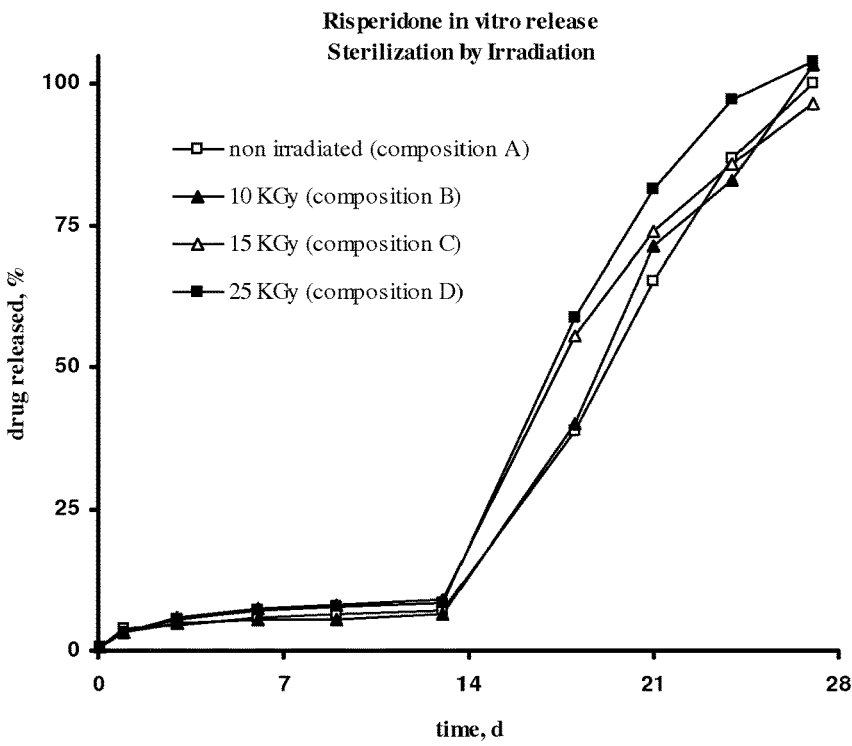
FIG. 40 depicts the release profile of Risperidone from implants prepared according to Example 15. Results are expressed as % Risperidone released from implants as a function of time.
Figure 41:
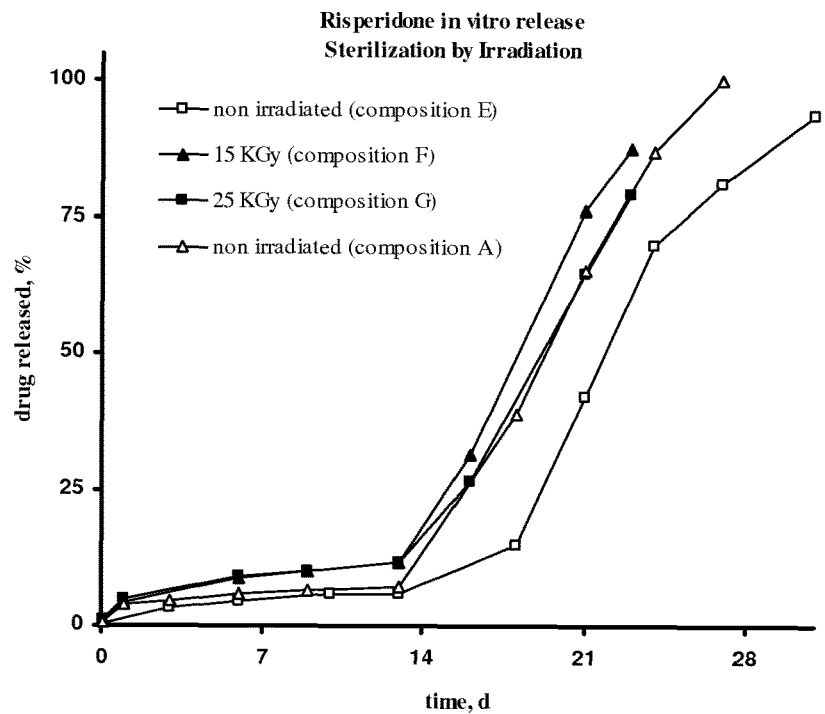
FIG. 41 depicts the release profile of Risperidone from implants prepared according to Example 15. Results are expressed as % Risperidone released from implants as a function of time.

In Vitro Release Profile:

The drug released from compositions of this example was evaluated according to the following procedure: The amount of formulation corresponding to 25 mg of risperidone was injected from prefilled syringes into flasks having a pre-warmed release medium by using a 21 G needle. The release medium was 250 ml phosphate buffer pH=7.4. The flasks were then placed into an oven at 37° C. and kept under horizontal shaking at 50 rpm. At previously scheduled time points (2 h, 1 d, and periodically up to 28 days), 5 ml of release medium was collected and replaced with fresh buffer and the amount of risperidone present in the sample was determined by UV spectrophotometry. The profile of risperidone released from the implants of this example is shown in FIG. 40 and FIG. 41. The results are expressed as % drug released from implants as a function of time.

As depicted in FIG. 40, the release of the risperidone from the same formulation either non irradiated (composition A) or irradiated at different levels (compositions B, C and D) in the range 5-25 KGy resulted in very similar profiles because the inherent viscosity of the polymer and the viscosity of the polymer solution were still within the preferred range of 0.20-0.50 dL/g and 0.20 to 7 Pa·s, respectively. FIG. 41 shows how the other polymer with a higher Mw (39,708 g/mol) (composition E) which presents an slightly slower release profile, once it is irradiated (compositions F and G) presents a release profile closer to the non-irradiated lower Mw polymer (composition A), due to the loss of molecular weight during sterilization process, which leads to a composition with a polymer inherent viscosity and polymer solution viscosity inside preferred ranges.

In Vivo Plasma Levels after Intramuscular Administration to New Zealand Rabbit:

The risperidone compositions A, B, C, D and G of this example were injected intramuscularly to New Zealand White rabbits weighing an average of 3 kg. The amount injected corresponded to a dose of 15 mg risperidone, and the composition was placed intramuscularly in the left hind leg using a syringe with a 20 G needle. The total number of rabbits per composition was 3. After injection, plasma levels were obtained at 0, 4 h, 1 d, 2 d, 5 d, 7 d, 10 d and periodically up to 28 days.

Figure 42:
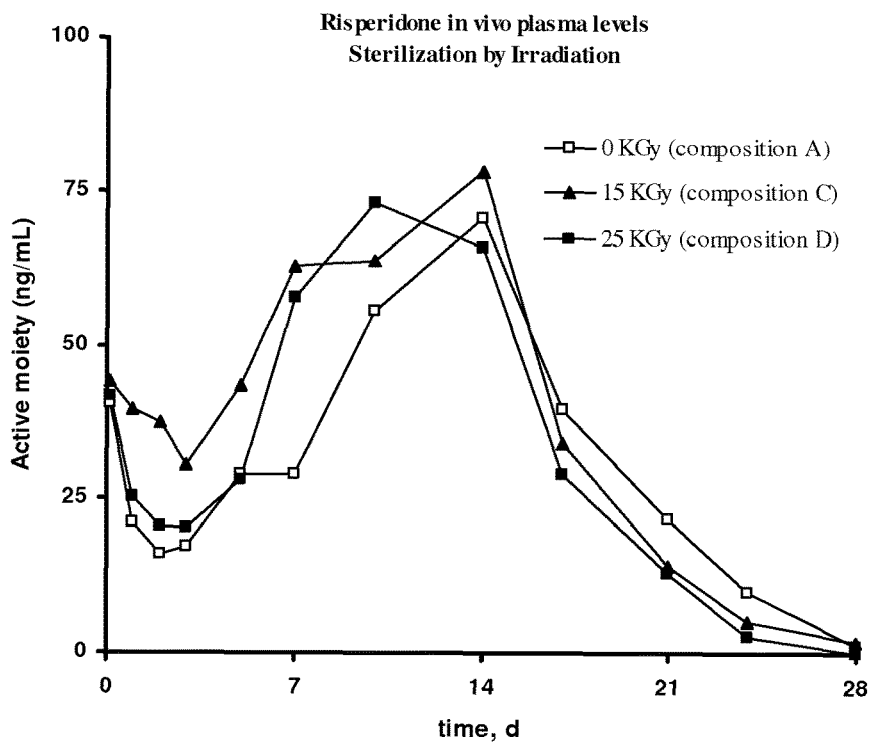
FIG. 42 depicts the plasma level profile of Risperidone in New Zealand rabbits provided by implants prepared according to Example 15. Results are expressed as the sum of the concentrations of Risperidone and its active metabolite 9-hydroxide-risperidone as a function of time.
Figure 43:
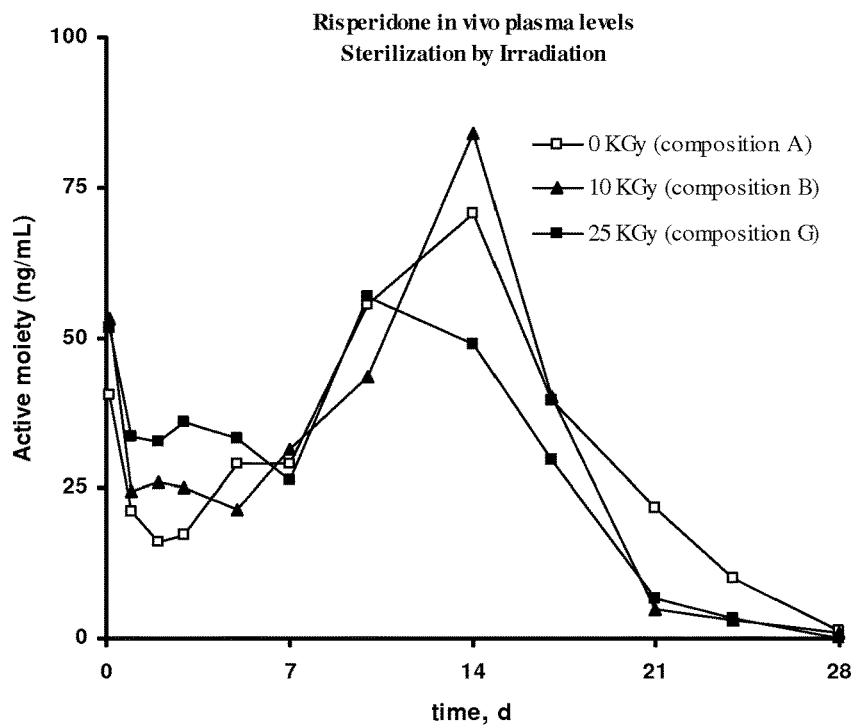
FIG. 43 depicts the plasma level profile of Risperidone in New Zealand rabbits provided by implants prepared according to Example 15. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 42 and FIG. 43. The results are expressed as the sum of the risperidone plus 9-OH-risperidone concentrations (ng/ml) as a function of time, since the therapeutic activity of 9-OH-risperidone is substantially equivalent to that of risperidone. As it can be observed in these Figures, the injection of an amount of composition equivalent to 15 mg risperidone to New Zealand White rabbits resulted on very similar plasma levels as could be predicted since in vitro behaviour was very similar after irradiation. FIGS. 42 and 43 revealed not substantial changes in the plasma levels of the risperidone active moiety when a formulation comprising 27,020 g/mol mean molecular weight polymer was irradiated at 10, 15 and 25 KGy, because key parameters such as the inherent viscosity of the polymer and the viscosity of the polymeric solution viscosity are still within the previously determined preferred range of 0.20-0.50 dL/g and 0.20 to 7 Pa·s, respectively.

A higher molecular weight polymer (39,708 g/mol), with inherent viscosity out of the preferable range (0.58 dL/g), once it is irradiated at 25 KGy (since higher molecular weight polymers suffered proportionally higher molecular weight losses during irradiation), led to a polymer with inherent viscosity within the preferred range and an still adequate viscosity of the polymer solution of 1.78 dL/g. The higher molecular weight polymer after 25 KGy irradiation resulted extremely close to the non-irradiated lower one (27,020 g/mol), thereby allowing adequate long lasting implantable systems, and experimenting a very similar in vivo behaviour (plasma levels profile) as observed in FIG. 43.

Example 16: Study of Reconstitution of the Formulations

Risperidone implantable formulations were prepared with the following composition:

| Component | Amount (mg) |
| --- | --- |
| PLGA polymer | 50 |
| Risperidone | 25 |
| Dimethyl sulfoxide (solvent) | 116.7 |

Polymer corresponds to a 50:50 lactic/glycolic, inherent viscosity 0.40 dL/g polymer. The risperidone selected for the compositions of this example showed a usual particle size distribution between 10-225 microns (not more than 10% of drug particles with a particle size smaller than 10 microns, and not more than 10% larger than 225 microns). Three different methods were applied to reconstitute the composition:

A) Vial. The polymeric solution was prepared by weighing the appropriate amounts of polymer and solvent and mixing them by vortexing until the polymer had completely dissolved in the solvent. Then, the appropriate risperidone amount was added to the polymeric solution and an homogeneous suspension was obtained by vortexing.

B) Syringes. The risperidone, the polymer and the solvent were weighed independently in glass syringes. The polymeric solution was then prepared by connecting the respective syringes by a fluid connector so that the solvent was moved from the syringe containing it to the syringe containing the polymer and then making several forward-backward cycles from one syringe to the other by pushing the respective plungers. Once the polymer is completely dissolved in the solvent, the third syringe containing the risperidone was connected and an homogeneous suspension was then obtained by doing several additional cycles.

C) Freeze-drying. Polymer and risperidone were freeze-dried in a prefilled glass syringe and the solvent was placed in a second syringe. The syringes were connected by a fluid connector and then the solvent was moved to the syringe containing the freeze-dried polymer-risperidone mixture and finally several forward-backward cycles were repeated until a homogeneous suspension was achieved.

Preparation methods B and C can also be carried out by direct connection of syringes using female-male luer syringes.

In Vitro Release Profile:

The risperidone released from formulations corresponding to the 3 methods was evaluated according to the following procedure: the amount of formulation corresponding to 25 mg of risperidone was injected from prefilled syringes into flasks by using a 21 G needle followed by the careful addition of a pre-warmed release medium. The release medium was 250 ml phosphate buffer pH=7.4. The flasks were then placed into an oven at 37° C. and kept under horizontal shaking at 50 rpm. At previously scheduled time (2 h, 1 d, 3 d, 7 d, 10 d, 14 d, 17 d, 21 d, 24 d, 28 d, 31 d and 35 d), 5 ml of release medium was collected and replaced with fresh buffer, and the amount of risperidone amount present in the sample was determined by UV spectrophotometry.

Figure 44:
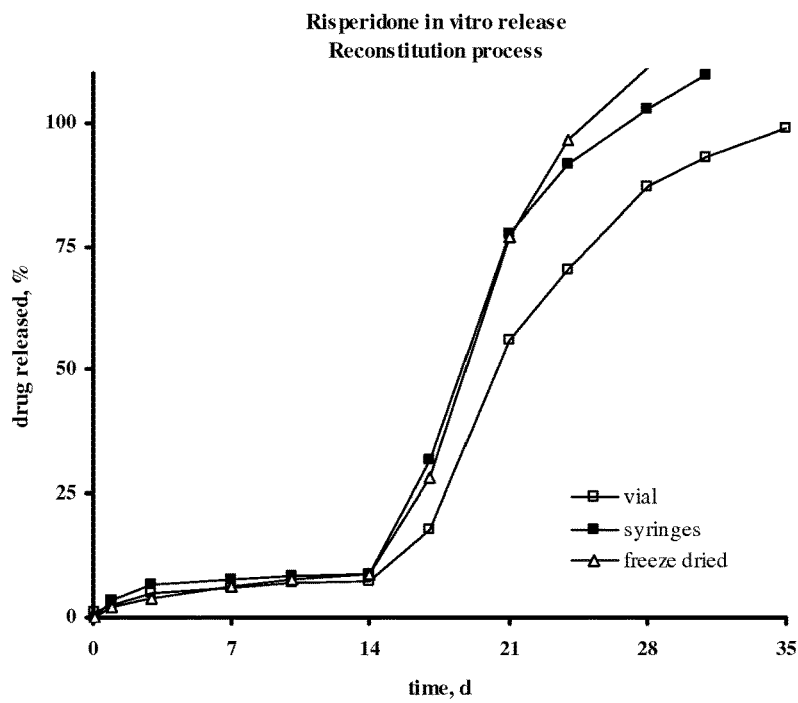
FIG. 44 depicts the release profile of Risperidone from implants prepared according to Example 16. Results are expressed as % Risperidone released from implants as a function of time.

The profile of risperidone released from the implants is shown in FIG. 44. The results are expressed as % Risperidone released from the formulation as a function of time. As it can be observed in FIG. 44, the release profile of the implantable formulations prepared by the three different methods was the same during first 2 weeks. However, after 14 days the preparation method A (vial) resulted in a slightly slower release rate, probably due the higher porosity of the implants formed by the other 2 methods because of the air introduced to the formulation during the reconstitution process.

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. The total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 45:
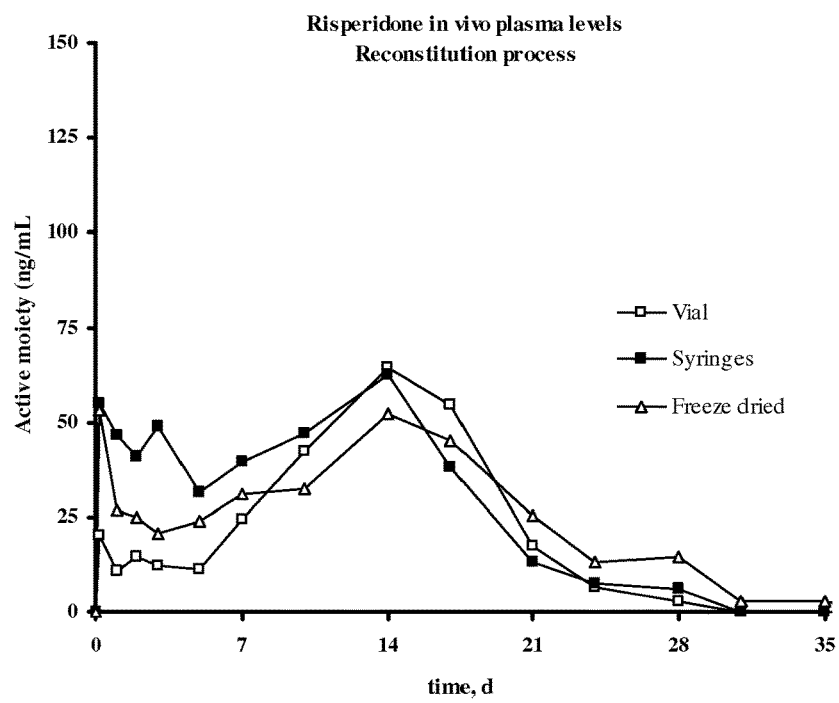
FIG. 45 depicts the plasma level profile of Risperidone in New Zealand rabbits provided by implants prepared according to Example 16. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 45. The results are expressed as the sum of the risperidone plus 9-OH-risperidone concentrations (ng/ml) as a function of time, since the therapeutic activity of 9-OH-risperidone is substantially equivalent to that of risperidone. As it can be seen in the cited Figure, the injection of an amount of formulation corresponding to 15 mg risperidone to New Zealand White rabbits resulted in initial plasma levels starting from 4 h post-administration up to at least 28 days. The methods consisting on reconstitution of a formulation pre-filled in different containers by their mixing (Methods B and C) evoked slightly higher initial plasma levels. This could be due to the higher porosity, and consequently higher initial diffusion, of the implantable formulations prepared by these two methods in comparison with Method A (preparation inside a vial). This fact could be also the reason for their higher plasma levels during the first week after administration.

In Vivo Plasma Levels after Intramuscular Administration to Beagle Dog

The risperidone formulations of this example were also injected intramuscularly to Beagle dogs weighing an average of 10 kg. The amount injected corresponded to a dose of 25 mg risperidone and the composition was placed intramuscularly in the left hind leg using a syringe with a 20 G needle. Total number of dogs was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 46:
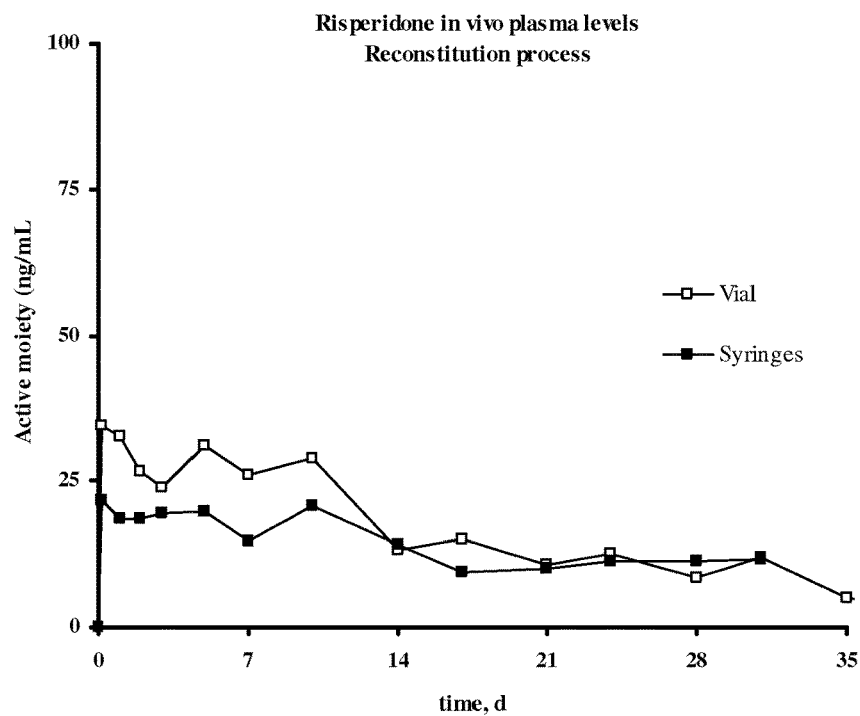
FIG. 46 depicts the plasma level profile of Risperidone in Beagle dogs provided by implants prepared according to Example 16. Results are expressed as the sum of the concentrations of Risperidone and its active metabolite 9-hydroxide-risperidone as a function of time.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 46. The results are expressed as the sum of the risperidone plus 9-OH-risperidone concentrations (ng/ml) as a function of time, since the therapeutic activity of 9-OH-risperidone is substantially equivalent to that of risperidone. As it can be seen in the cited Figure, the injection of an amount of formulation corresponding to 25 mg risperidone to Beagle dogs resulted in well-controlled initial plasma levels with sustained and similar levels up to at least 35 days using different preparation methods such as prior elaboration of polymeric solution followed by drug addition (vial, method A) or by direct reconstitution starting from solid components (syringes, method B).

The above experiments clearly demonstrate that, in an injectable depot composition intended to release a drug contained therein, the initial burst release of the drug can be satisfactorily controlled by controlling at least one of the following factors:

the viscosity of the polymeric solution;
the intrinsic or inherent viscosity ($\eta_{inh}$) of the polymer; and
the water solubility of the drug.

By adequately controlling at least one of these factors, the release of the drug from the implant can be precisely controlled during at least the first 14 days and up to 6 months following a single administration. The injectable compositions of the invention can therefore form a suspension/dissolution/dispersion within a biodegradable and biocompatible polymeric solution that can be parenterally administered for example by means of a syringe and a needle and which solidifies inside the body by solvent diffusion, thereby forming the implant.

As used herein, the term about is taken to mean±10%, ±5% or ±1% of a specified value.

The invention claimed is:

1. An injectable depot composition consisting of risperidone, and a polymeric solution of DMSO and PLGA copolymer, wherein:
   the content of risperidone is 13% wt±10%, based upon the weight of the composition, and the risperidone possesses a particle distribution selected from:
   a. not more than 10% of the total volume of the particles is smaller than 10 microns, not more than the 10% of the total volume of particles is greater than 225 microns, and the d0.5 is in the range of 10-200 microns;
   b. not more than 10% of the total volume of the particles is less than the range 1-10 µm, not more than the 10% of the total volume of particles is greater than the range 225-400 µm, and the d0.5 of the size distribution is in the range of about 40-200 µm; or
   c. expressed as volume, d0.9 is about 150 to about 400 µm, d0.5 is about 40 to about 200 µm and d0.1 is about 10 to about 60 µm;
   the mass ratio of DMSO to risperidone is 4.66±10%:1;
   the mass ratio of polymeric solution to risperidone is about 6.66±10%:1;
   the PLGA copolymer is an end-capped biodegradable poly(lactide-co-glycolide) copolymer having a monomer ratio of lactic acid to glycolic acid of 50:50 and an inherent viscosity in the range of 0.20±10% dl/g to 0.50±10% dl/g as measured in chloroform at 25° C. at a concentration of 0.1% wt/v with a Ubbelohde size 0c glass capillary viscometer;
   the polymeric solution has a viscosity in the range of 0.5-3.0 Pa·s; and
   the amount of risperidone dissolved in the injectable composition is 20% wt.

2. The injectable depot composition according to claim 1, wherein the composition is a sterilized composition.

3. The injectable depot composition according to claim 2, wherein the sterilization has been carried out by sterilizing at least one of the drug and the biocompatible polymer by beta-irradiation in the range 5-25 KGy.

4. A pharmaceutical kit suitable for preparation of the injectable depot composition according to claim 1, the kit comprising:
   a first container comprising the PLGA copolymer; and
   a second container comprising the DMSO; and
   wherein the risperidone is present in the first container, second container or a third container,
   whereby mixing of the PLGA copolymer, DMSO and risperidone results in formation of the injectable depot composition.

5. The injectable depot composition according to claim 1, wherein the viscosity of the injectable composition is in the range of about 0.7 Pa·s to about 4.0 Pa·s.

6. The injectable depot composition according to claim 1, wherein
   a) the PLGA copolymer has been exposed to 5 to 25 KGy of beta-radiation sufficient to sterilize the PLGA copolymer prior to inclusion in the injectable composition or prior to addition of the DMSO; or
   b) the PLGA copolymer has been exposed to 10-25 KGy of beta-radiation sufficient to reduce the molecular weight of the PLGA copolymer prior to inclusion in the injectable composition or prior to addition of the DMSO, and thereby the intrinsic viscosity thereof.

7. The injectable depot composition according to claim 1, wherein the composition is injectable by hand through a 18 to 22 gauge needle.

8. The injectable depot composition according to claim 1, wherein the composition forms a biodegradable solid single body implant in situ in a subject to which it is administered.

9. The injectable depot composition of claim 1, wherein the composition releases at least 0.5% wt and no more than 8% wt of its charge of risperidone within 24 hours after being placed in an aqueous environment.

10. The injectable depot composition of claim 1, wherein the composition provides a substantially level plasma profile, for the risperidone, and/or metabolite thereof, of within ±15% of the average or mean during a period of at least 14 days following administration of the composition to a subject, wherein the average or mean is calculated over the 14 days.

11. The injectable depot composition of claim 10, wherein the composition provides a plasma profile, for the risperidone, and/or metabolite thereof, defined as follows:

| Dose (mg) | Cmin (ng/ml) | Cavg (ng/ml) | Cmax (ng/ml) |
|---|---|---|---|
| 25-150 | 1-80 | 3-200 | 8-300 | during a dosing period of at least 14 days following administration to a subject of an amount of the injectable composition equivalent to the dose indicated.

12. The injectable depot composition of claim 1, wherein the composition provides a substantially level plasma profile, for the risperidone, and/or metabolite thereof, of within ±20% of the average or mean during a dosing period of at least 28 days following administration of the composition to a subject, wherein the average or mean is calculated over the 28 days.

13. The injectable depot composition of claim 1, wherein the composition provides a substantially level plasma profile, for the risperidone, and/or metabolite thereof, of within ±10% of the average or mean during a period of at least 14 days following administration of the composition to a subject, wherein the average or mean is calculated over the 14 days.

* * * * *

UNITED STATES PATENT AND TRADEMARK OFFICE
CERTIFICATE OF CORRECTION

PATENT NO. : 10,058,504 B2
APPLICATION NO. : 13/690707
DATED : August 28, 2018
INVENTOR(S) : Ibon Gutierro Aduriz and Maria Teresa Gomez Ochoa Page 1 of 1

It is certified that error appears in the above-identified patent and that said Letters Patent is hereby corrected as shown below:

On the Title Page

Below Item (65), insert:
-- (63) Related U.S. Application Data
Continuation-in-part of Application No. PCT/EP2011/059001,
filed on May 31, 2011 --

In the Claims

Column 44, Claim 1, Line 67, correct text as follows:
"composition is ≤20% wt."

Signed and Sealed this
Twenty-fifth Day of December, 2018

Andrei Iancu
*Director of the United States Patent and Trademark Office*